(12) United States Patent
Choi et al.

(10) Patent No.: US 12,272,029 B2
(45) Date of Patent: Apr. 8, 2025

(54) X-RAY IMAGING DEVICE AND X-RAY IMAGING METHOD

(71) Applicant: DRTECH CORPORATION, Seongnam-si (KR)

(72) Inventors: Il Woong Choi, Seoul (KR); Choul Woo Shin, Seongnam-si (KR); Mi Jung Jo, Suwon-si (KR); Won Taek Seo, Seongnam-si (KR)

(73) Assignee: DRTECH CORPORATION, Seongnam-si (KR)

( * ) Notice: Subject to any disclaimer, the term of this patent is extended or adjusted under 35 U.S.C. 154(b) by 358 days.

(21) Appl. No.: 17/900,944

(22) Filed: Sep. 1, 2022

(65) Prior Publication Data
US 2023/0325993 A1 Oct. 12, 2023

(30) Foreign Application Priority Data

Apr. 11, 2022 (KR) .......................... 10-2022-0044502

(51) Int. Cl.
*G06T 5/50* (2006.01)
*A61B 6/50* (2024.01)
(Continued)

(52) U.S. Cl.
CPC .............. *G06T 5/50* (2013.01); *A61B 6/505* (2013.01); *G06T 7/0012* (2013.01); *G06T 7/13* (2017.01);
(Continued)

(58) Field of Classification Search
CPC .. G06T 5/50; G06T 7/254; G06T 7/13; G06T 7/0012; G06T 2207/10116;
(Continued)

(56) References Cited

U.S. PATENT DOCUMENTS

| 8,315,355 | B2 | 11/2012 | Mohamed |
| 2003/0216631 | A1* | 11/2003 | Bloch .................... G06T 3/153 |
| | | | 600/407 |

(Continued)

FOREIGN PATENT DOCUMENTS

| JP | 2016537099 A | 12/2016 |
| JP | 6549561 B2 | 7/2019 |

(Continued)

OTHER PUBLICATIONS

International Search Report dated Jan. 5, 2023, in the counterpart Korean Patent Application No. PCT/KR2022/009029.

(Continued)

*Primary Examiner* — Jamares Q Washington
(74) *Attorney, Agent, or Firm* — Rabin & Berdo, P.C.

(57) ABSTRACT

An X-ray imaging device includes an X-ray irradiation module, an X-ray detection module and an image processor. The image processor is configured to perform: acquiring a high-energy image and a low-energy image respectively obtained by X-ray of relatively high-energy and X-ray of relatively low-energy; generating high-energy frequency component images for each of a plurality of frequency bands by decomposing the high-energy image; generating low-energy frequency component images for each of a plurality of frequency bands by decomposing the low-energy image; generating merged frequency component images by merging at least a portion of the high-energy frequency component images for each of the plurality of frequency bands and at least a portion of the low-energy frequency component images for each of the plurality of frequency bands; and generating a standard image using the merged frequency component images.

15 Claims, 15 Drawing Sheets

(51) Int. Cl.
  *G06T 7/00* (2017.01)
  *G06T 7/13* (2017.01)
  *G06T 7/254* (2017.01)
  *G06T 7/30* (2017.01)
  *G06T 7/70* (2017.01)

(52) U.S. Cl.
  CPC ............... *G06T 7/254* (2017.01); *G06T 7/30* (2017.01); *G06T 7/70* (2017.01); *G06T 2207/10116* (2013.01); *G06T 2207/20016* (2013.01); *G06T 2207/20056* (2013.01); *G06T 2207/20064* (2013.01); *G06T 2207/20221* (2013.01); *G06T 2207/20224* (2013.01); *G06T 2207/30008* (2013.01)

(58) Field of Classification Search
  CPC . G06T 2207/20221; G06T 2207/20224; G06T 2207/30008; A61B 6/505
  USPC ............. 382/128, 130, 132, 190, 266; 378/5
  See application file for complete search history.

(56) References Cited

U.S. PATENT DOCUMENTS

| | | | |
|---|---|---|---|
| 2010/0046822 | A1 | 2/2010 | Li et al. |
| 2014/0243579 | A1 | 8/2014 | Roeske et al. |
| 2016/0267651 | A1* | 9/2016 | Maack ................. A61B 6/5258 |
| 2016/0350910 | A1* | 12/2016 | Jeong ..................... A61B 6/482 |
| 2021/0267563 | A1* | 9/2021 | Sattarivand ............... G06T 5/70 |

FOREIGN PATENT DOCUMENTS

| | | | |
|---|---|---|---|
| JP | 6681864 | B2 | 4/2020 |
| JP | 2021129717 | A | 9/2021 |
| KR | 20110111955 | A | 10/2011 |
| KR | 20130142654 | A | 12/2013 |
| KR | 10-1501086 | B1 | 3/2015 |
| KR | 20160139163 | A | 12/2016 |

OTHER PUBLICATIONS

Korean Office Action dated Feb. 2, 2024, in the counterpart Korean Patent Application No. 10-2022-0044502.

* cited by examiner (a)          (b)

(a)                    (b)

(a)            (b)

(a)            (d)

(b)            (c)

FIG. 10
(a)
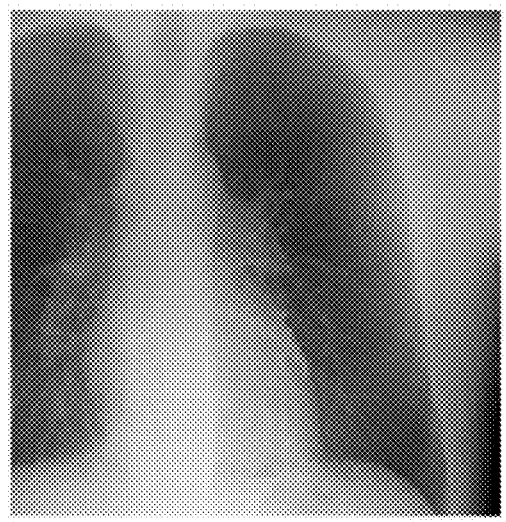
(b)

(a)　　　　　　　　　　　(b)

FIG. 15
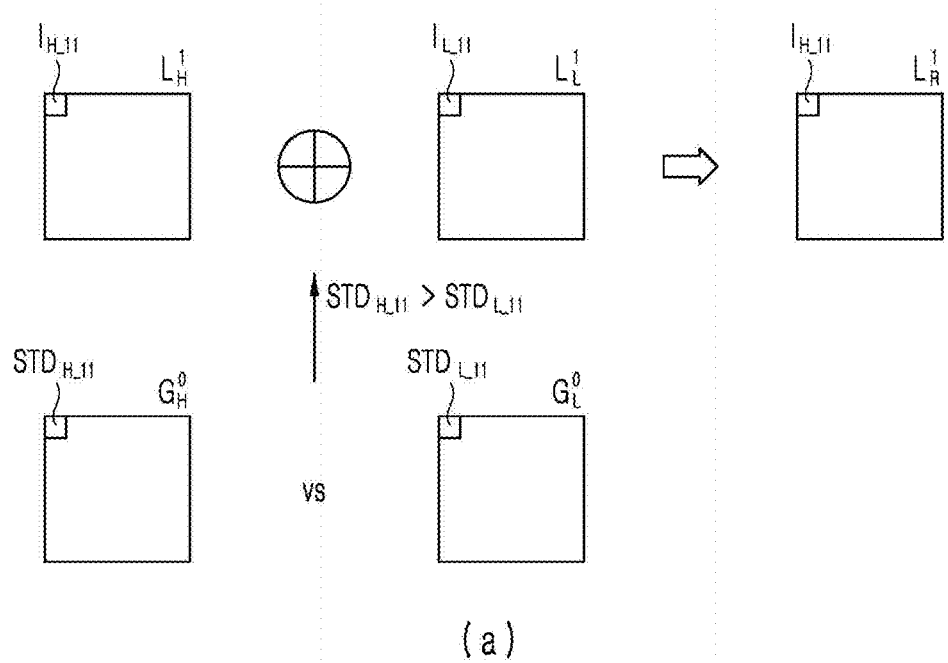
(a)
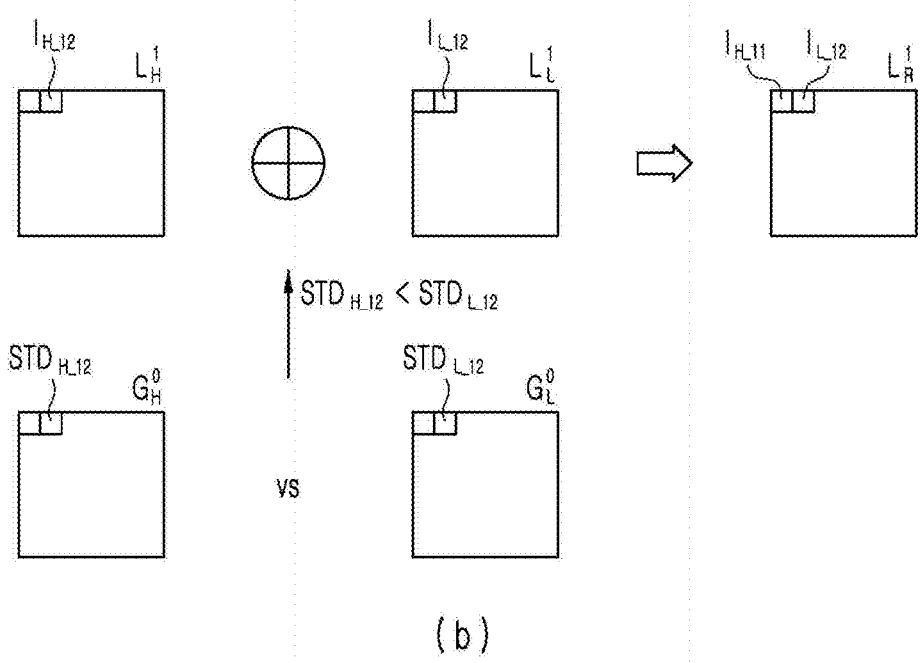
(b)

X-RAY IMAGING DEVICE AND X-RAY IMAGING METHOD

CROSS-REFERENCE TO RELATED APPLICATIONS

This application claims the benefit under 35 USC 119(a) of Korean Patent Application No. 10-2022-0044502, filed on Apr. 11, 2022, in the Korean Intellectual Property Office, the entire disclosure of which is incorporated herein by reference for all purposes.

TECHNICAL FIELD

The present invention relates to an X-ray imaging device obtaining images using X-ray and an X-ray imaging method using the same.

BACKGROUND ART

An X-ray imaging device is an imaging device that irradiates X-ray to a target part of a human body or an animal body and receives the transmitted X-ray to obtain an image of the target part. Such an X-ray imaging device steadily or continuously provides an X-ray image of a target part and is widely used for diagnosis of a target part or various medical treatments.

A DES (Dual Energy Subtraction) technology is used as an image processing technique for generating images obtained by separating and extracting soft tissue and bone from a digital X-ray image of a body part, for example, a chest. The DES has been widely used to improve the diagnostic accuracy of the chest, especially. The DES technology is based on the difference in attenuation of low-energy and high-energy X-rays of soft tissue and bone and generates respectively a soft tissue image and a bone image by removing parts corresponding to bones and soft tissues of an X-ray image of a chest through a calculation of ratio of the difference in attenuation of X-ray under low-energy and high-energy conditions for each material. In general, removing a specific part from an X-ray image is called a subtraction.

Soft tissue images and bone images obtained by DES enable accurate diagnosis of lesions with improved visibility compared to conventional chest X-ray images. The two-shot photographing of the dual energy X-ray image used in the DES processing is performed by irradiating high-energy and low-energy X-rays to the subject at intervals of several hundred milliseconds (msec), and thus a motion artifact may occur in a subtracted image due to position changes in images caused by the motion of the subject. For this reason, although in the case of two-shot photographing a photographing is performed while fixing the subject in order to reduce the motion artifact, large changes occur in the heart, the pulmonary blood vessels or the like and thereby the motion artifacts inevitably appear, which deteriorates the image quality to interfere with the diagnosis.

PRIOR ART DOCUMENTS

Korean Patent Registration No. 10-1501086 (2015 Mar. 4)
Japanese Patent Registration JP JP6549561 B (2019 Jul. 5)
U.S. Pat. No. 8,315,355B (2012 Nov. 20)

SUMMARY

An object of the present invention is to provide a method for reducing motion artifact of an image generated by subtraction image processing in order to improve the accuracy of image diagnosis.

Another object to be solved by the present invention is to provide a method for improving the image quality of a standard image, a soft tissue image and a bone image obtained by irradiating dual energy X-rays.

An X-ray imaging device according to an embodiment of the present invention includes: an X-ray irradiation module configured to irradiate X-ray; an X-ray detection module configured to detect X-ray passed through an object after being irradiated from the X-ray irradiation module to output a corresponding digital signal; and an image processor configured to generate an X-ray image using an output signal of the X-ray detection module. The image processor is configured to perform: acquiring a high-energy image and a low-energy image respectively obtained by X-ray of relatively high-energy and X-ray of relatively low-energy; generating high-energy frequency component images for each of a plurality of frequency bands by decomposing the high-energy image; generating low-energy frequency component images for each of a plurality of frequency bands by decomposing the low-energy image; generating merged frequency component images by merging at least a portion of the high-energy frequency component images for each of the plurality of frequency bands and at least a portion of the low-energy frequency component images for each of the plurality of frequency bands; and generating a standard image using the merged frequency component images.

The high-energy frequency component images for the plurality of frequency bands may include high-energy Laplacian pyramid images of a plurality of frequency band levels and high-energy Gaussian pyramid image of a plurality of frequency band levels, and the low-energy frequency component images for the plurality of frequency bands may include low-energy Laplacian pyramid images of a plurality of frequency band levels and low-energy Gaussian pyramid image of a plurality of frequency band levels. The merged frequency component image may be generated by merging the high-energy Laplacian pyramid images and the low-energy Laplacian pyramid image for each frequency band level.

The high-energy Laplacian pyramid image and the low-energy Laplacian pyramid image may be merged with each other for a pixel for each level or for a patch having a plurality of pixels. When the high-energy Laplacian pyramid image and the low-energy Laplacian pyramid image are merged for each level, the merging may be performed by selecting a pixel or a patch of one of the high-energy Gaussian pyramid image and the low-energy Gaussian pyramid image of the corresponding level that has a statistical value indicating a higher contrast, or a pixel or a patch of one of the high-energy Laplacian pyramid image and the low-energy Laplacian pyramid image that has a statistical value indicating a higher contrast.

When the merging is performed based on a comparison of statistical values of the corresponding patches of the high-energy Gaussian pyramid image and the low-energy Gaussian pyramid image, the statistical value indicating the contrast may be a standard deviation or an average of absolute deviations of brightness values of the plurality of pixels constituting the corresponding patch. When the merging is performed based on a comparison of statistical values of the corresponding patches of the high-energy Laplacian pyramid image and the low-energy Laplacian pyramid image, the statistical value indicating the contrast may be a standard deviation or an average of absolute deviations of brightness values of the plurality of pixels constituting the corresponding patch.

The high-energy frequency component images for each of the plurality of frequency bands may include high-energy frequency component images for each of the plurality of frequency bands decomposed by a Fourier transform or a wavelet transform, and the low-energy frequency component images for each of the plurality of frequency bands may include a plurality of low-energy frequency component images for each frequency bands decomposed by a Fourier transform or a wavelet transform. The merged frequency component image may be generated by the merging of the high-energy frequency component image and the low-energy frequency component image for each frequency band and an inverse Fourier transform or an inverse wavelet transform thereof.

The high-energy frequency component image and the low-energy frequency component image may be merged with each other for a pixel or for a patch having a plurality of pixels. When the high-energy frequency component image and the low-energy frequency component image are merged for each frequency band, the merging may be performed by selecting a pixel or a pixel patch of one of the high-energy frequency component and the low-energy frequency component of the corresponding frequency band that has a statistical value indicating a greater contrast to be merged.

When the merging is performed based on the comparison of the statistical values of the corresponding patches of the high-energy frequency component image and the low-energy frequency component image, the statistical value representing the contrast may be an average or a median of absolute values of a plurality of pixel values constituting the corresponding patch.

The standard image may be generated by merging frequency component images for a plurality of frequency bands constituting the merged frequency component image.

The image processor may be configured to further perform a step of performing an image registration at least one of the high-energy image and the low-energy image, and the image registration may include a plurality of image registrations that are performed respectively using a bone masking information and a soft tissue masking information to reflect a difference of motions of the bone and the soft tissues.

The performing an image registration may include: generating a bone image and a soft tissue image by subtraction of the high-energy image and the low-energy image, respectively; generating a bone masking image including bone masking information and a soft tissue masking image from the generated bone image and the generated soft tissue image, respectively; firstly registering at least one of the high-energy image and the low-energy image to be registered using the bone masking image, and additionally registering at least one of the firstly registered high-energy image and the low-energy image using the soft tissue masking image.

The bone masking image may include an edge position information of a bone contained in the bone image, and the soft tissue masking image may include an edge position information of a soft tissue contained in the soft tissue image.

The firstly registering using the bone masking image uses a global optimization-based image registration algorithm.

The image registration algorithm may be an image registration algorithm that focuses on the motion of a bone in a Free-Form Deformation (FFD) method.

The additionally registering using the soft tissue masking image may be performed by locally registering by measuring a similarity of the high-energy image and the low-energy image in a patch including a predetermined number of pixels.

The may be measured through pixel values or information entropy between the high-energy image and the low-energy image.

The similarity may be measured using at least one of NCC (Normalized Cross Correlation) and MI (Mutual Information).

An X-ray imaging device according to another embodiment of the present invention includes: an X-ray irradiation module configured to irradiate X-ray; an X-ray detection module configured to detect X-ray passed through an object after being irradiated from the X-ray irradiation module to output a corresponding digital signal; and an image processor configured to generate an X-ray image using an output signal of the X-ray detection module. The image processor is configured to perform: acquiring a high-energy image and a low-energy image respectively obtained by X-ray of relatively high-energy and X-ray of relatively low-energy; performing an image registration for at least one of the high-energy image and the low-energy image; and generating at least one of a standard image, a bone image and a soft tissue image through a calculation using the high-energy image and the low-energy image that have undergone the image registration. The image registration comprises a plurality of image registrations performed using a bone masking information and a soft tissue masking information to reflect a difference of motions of the bone and the soft tissue.

An X-ray imaging method according to an embodiment of the present invention includes: irradiating X-ray to an object to be imaged; detecting X-ray passed through the object and generating a corresponding digital signal; and generating an X-ray image using the digital signal. The generating an X-ray image includes: acquiring a high-energy image and a low-energy image respectively obtained by X-ray of relatively high-energy and X-ray of relatively low-energy; generating high-energy frequency component images for each of a plurality of frequency bands by decomposing the high-energy image; generating low-energy frequency component images for each of a plurality of frequency bands by decomposing the low-energy image; generating merged frequency component images by merging at least a portion of the high-energy frequency component images for each of the plurality of frequency bands and at least a portion of the low-energy frequency component images for each of the plurality of frequency bands, and generating a standard image using the merged frequency component images.

An X-ray imaging method according to another embodiment of the present invention includes: irradiating X-ray onto an object to be imaged; detecting X-ray passed through the object and generating a corresponding digital signal; and generating an X-ray image using the digital signal. The generating an X-ray image includes: acquiring a high-energy image and a low-energy image respectively obtained by X-ray of relatively high-energy and X-ray of relatively low-energy; performing an image registration for at least one of the high-energy image and the low-energy image; and generating at least one of a standard image, a bone image and a soft tissue image through a calculation using the high-energy image and the low-energy image that have undergone the image registration. The image registration comprises a plurality of image registrations performed using a bone masking information and a soft tissue masking information to reflect a difference of motions of the bone and the soft tissue.

According to the present invention, motion noise of an image generated by subtraction image processing can be reduced. In addition, the image quality of a standard image, a soft tissue image and a bone image obtained by irradiating dual energy X-rays can be improved.

BRIEF DESCRIPTION OF DRAWINGS

FIG. 10 shows examples of images obtained by an image registration according to an embodiment of the present invention.

FIG. 15 is a drawing for explaining an integration in a pixel or patch unit when integrating high-energy Laplacian pyramid image and low-energy Laplacian pyramid image according to an embodiment of the present invention.

DETAILED DESCRIPTION

With reference to the accompanying drawings, the embodiments of the present invention will be described in detail so that a person of ordinary skill in the art to which the present invention pertains can easily implement them. However, the present invention may be embodied in many different forms and is not limited to the described embodiments.

Figure 1:
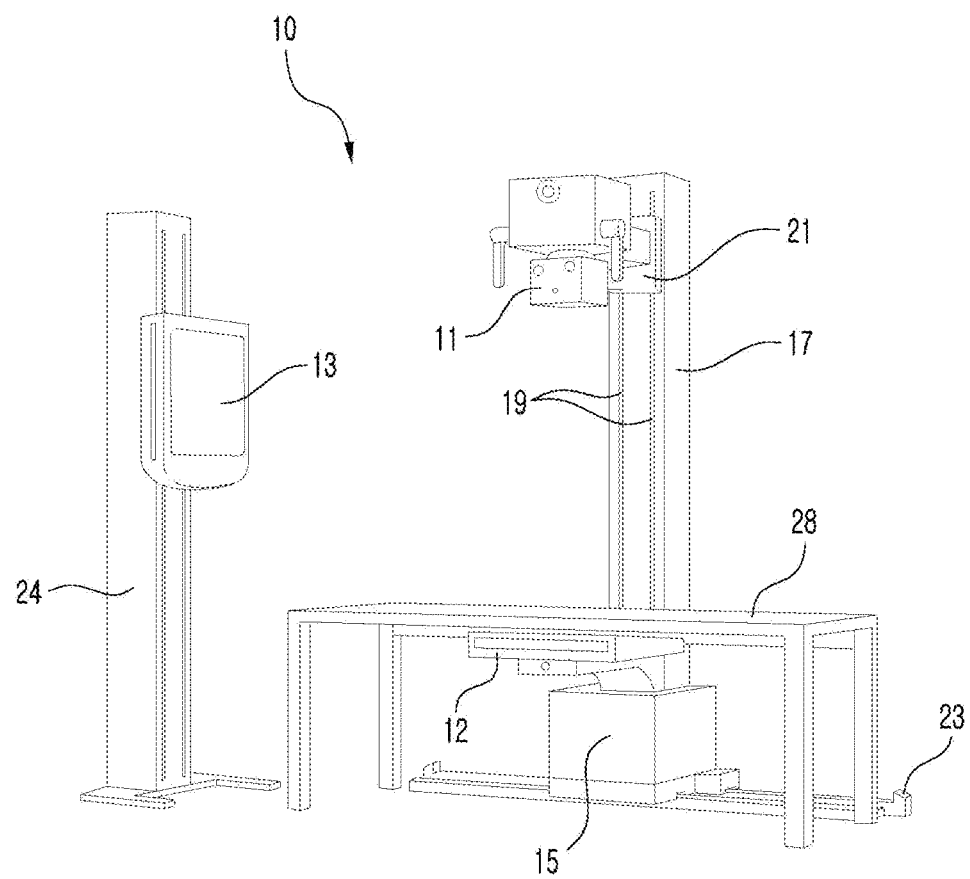
FIG. 1 schematically shows an X-ray imaging device according to an embodiment of the present invention.

FIG. 1 exemplarily shows an X-ray imaging device according to an embodiment of the present invention. Referring to FIG. 1, an X-ray imaging device 10 according to an embodiment of the present invention includes an X-ray irradiation module 11 that generates and irradiates X-rays, and X-ray detection modules 12 and 13 for detecting X-ray passing through a subject after being irradiated from the X-ray irradiation module 11. The X-ray detection modules 12 and 13 may include a first X-ray detection module 12 for implementing a bed type imaging structure and a second X-ray detection module 13 for implementing a stand type imaging structure. The X-ray irradiation module 11 is configured to be capable of undergoing linear movement and rotational movement so as to face any one of the first and second X-ray detection modules 12 and 13.

The X-ray irradiation module 11 may include an X-ray source that generates X-rays and generate X-rays with the electrical power supplied from a power module 15. A connection frame 17 extends upward on a power module 15 and may include guide grooves 19 for guiding the vertical movement of the X-ray irradiation module 11. The X-ray irradiation module 11 is fastened to the connection frame 17 in a vertically movable manner through the guide groove 19. At this time, a connection block 21 is connected to the connection frame 17 to be movable in the vertical direction, and the X-ray irradiation module 11 is supported by the connection block 21 to be able to move in the vertical direction together with the connection block 21. In addition, the X-ray irradiation module 11 may be supported by the connection block 21 to be rotatable about a horizontal axis. The power module 15 may be configured to be movable in a horizontal direction on a moving frame 23 extending in a horizontal direction. For example, the moving frame 23 may include a guide rail 25 extending in a horizontal direction, and the power module 15 may be positioned on the moving frame 23 to be movable in a horizontal direction through the guide rail 25.

The first X-ray detection module 12 may be installed in the connection frame 17 to face the X-ray irradiation module 11 in the vertical direction. X-ray imaging may be performed using the X-ray irradiation module 11 and the first X-ray detection module 12. A support table configured so that a subject, for example, a patient can be placed thereon may be disposed, and X-ray imaging may be performed in a state that the X-ray irradiation module 11 and the first X-ray detection module 12 are arranged to be positioned above and below the support table, respectively.

Meanwhile, the second X-ray detection module 13 may be supported on a separate stand 24 to be vertically movable. X-ray imaging may be performed using the X-ray irradiation module 11 and the second X-ray detection module 13. At this time, the X-ray irradiation module 11 rotates with respect to the connection block 21 and is aligned to face the second X-ray detection module 13, and X-ray imaging may be performed by the irradiation of X-ray from the X-ray irradiation module 11 and the detection of the X-ray having passed the patient in a state in which the patient is standing in close contact with the second X-ray detection module 13.

The first and second X-ray detection modules 12 and 13 may respectively include an X-ray detector for detecting X-rays, and the X-ray detector may have a storage type or a supporting type. In addition, the X-ray detector may be a cassette-type X-ray detector and may be accommodated in a receiving unit such as a bucky to be used when necessary. The cassette type digital X-ray detector may convert incident X-ray into electrical signals capable of image signal processing. For example, the X-ray detector may include a pixel circuit board including a thin film transistor and may include a plurality of switching cell elements and photoelectric conversion elements arranged in a matrix form. Here, the X-ray detector may be a direct type detector including a photoconductor having photoconductivity together with a pixel circuit board or an indirect type detector including a light emitting layer such as a scintillator, etc. together with a pixel circuit board.

Figure 2:
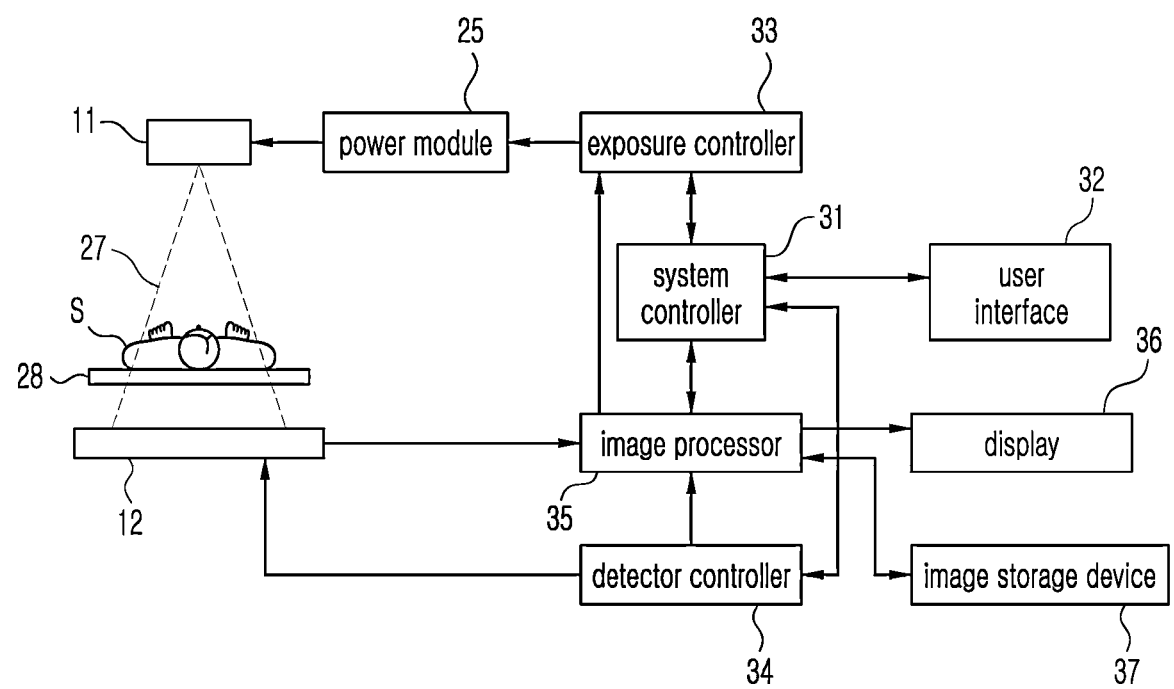
FIG. 2 is a block diagram of an X-ray imaging device according to an embodiment of the present invention.

FIG. 2 shows a schematic block diagram of an X-ray imaging device according to an embodiment of the present invention. The X-ray irradiation module 11 is configured to radiate the X-ray 27 toward a patient S lying on the table 28 that can transmit X-ray.

A system controller 31 controls the entire system, receives an image capturing command input through a user interface 32 such as a keyboard, a mouse, and a touch screen input device, and controls a process to be performed accordingly. When an image capturing command is input, the system controller 31 controls an exposure controller 33 that controls the operation of the power module 25, and the exposure controller 33 controls the power module 25 accordingly to irradiate the X-ray. Also, when an image capturing command is input, the system controller 31 outputs a signal for controlling a detector controller 34 for controlling the X-ray detection module 12. The system controller 31 outputs a signal corresponding to the input of the image capturing command to an image processor 35. In this case, the system controller 31 may transmit and receive necessary data to and from the exposure controller 33, the detector controller 34 and the image processor 35. The image processor 35 may receive necessary information from the detector controller 34 and transmit data necessary for image capturing to the exposure controller 33.

The X-ray detection module 12 detects X-ray having passed through the patient S after being irradiated from the X-ray irradiation module 11 and generates a digital signal corresponding to the detected X-ray. The image processor 35 generates an image by using the digital image signal received from the X-ray detection module 12. The image processing performed by the image processor 35 and an image obtained thereby will be described later.

A display 36 displays the image acquired by the image processor 35 and may be any display capable of displaying an image, such as a liquid crystal display device, an OLED display device, or the like. An image storage device 37 may be a memory capable of storing the acquired image and may be any type of memory, such as a memory, a database, a cloud storage device, or the like.

Figure 3:
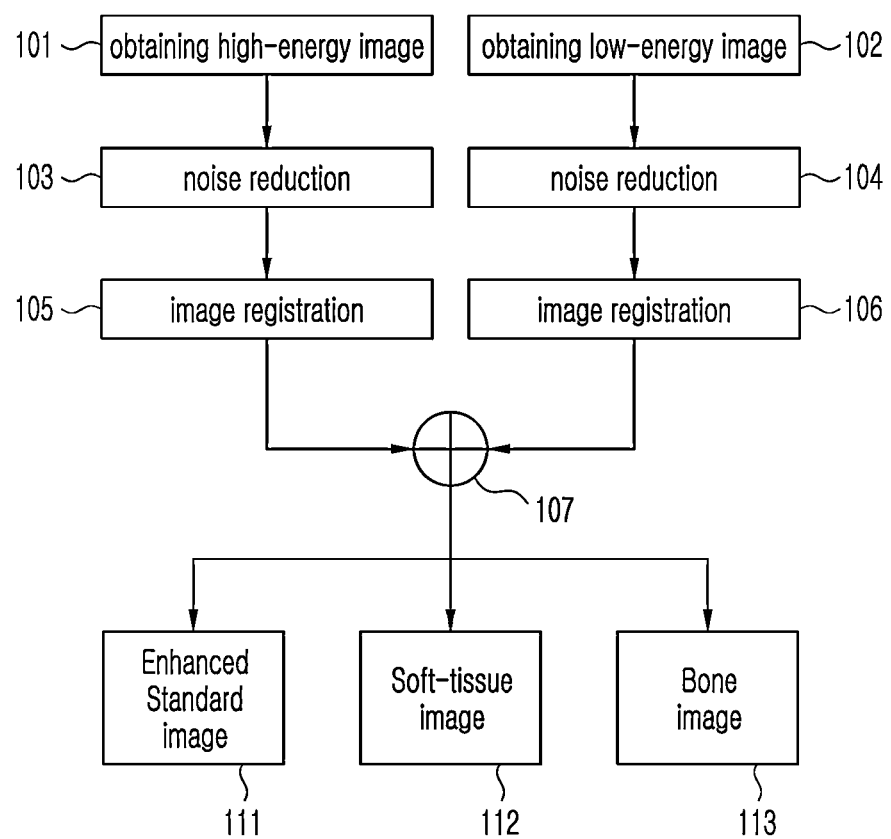
FIG. 3 is a flow chart schematically showing a dual energy subtraction image processing method according to an embodiment of the present invention.

FIG. 3 is a flowchart schematically illustrating a method of a dual energy subtraction image processing according to an embodiment of the present invention, and the image processor 35 may be configured to perform a dual energy subtraction image processing. The image processor 35 is configured to perform the image processing process described below and may include a microprocessor, a memory and related hardware and software.

Referring to FIG. 3, a high-energy image $I_H$ and a low-energy image $I_L$ are respectively obtained using dual energy, that is, high-energy and low-energy X-rays, respectively, in steps 101 and 102. For example, a high-energy image may be obtained by irradiating X-ray of relatively high-energy (of 120 kVp), and a low-energy image may be obtained by irradiating X-ray of relatively low-energy (of 60 kVp). Different images are obtained according to differences in mass attenuation coefficients of X-ray for soft tissue and bone under high-energy and low-energy conditions.

Figure 4:
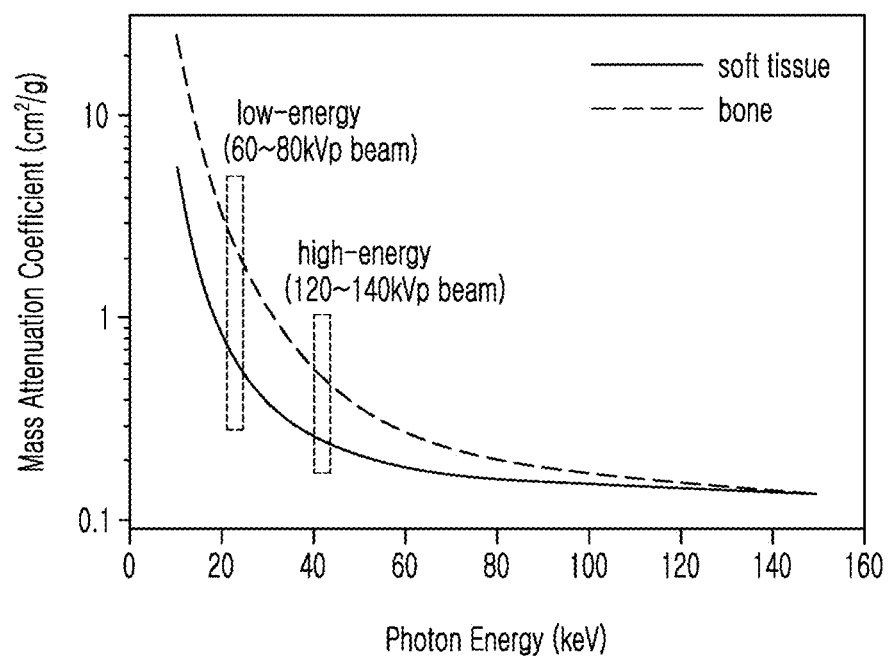
FIG. 4 shows graphs illustrating changes of a mass attenuation coefficient depending on the energy of an X-ray.
Figure 5:
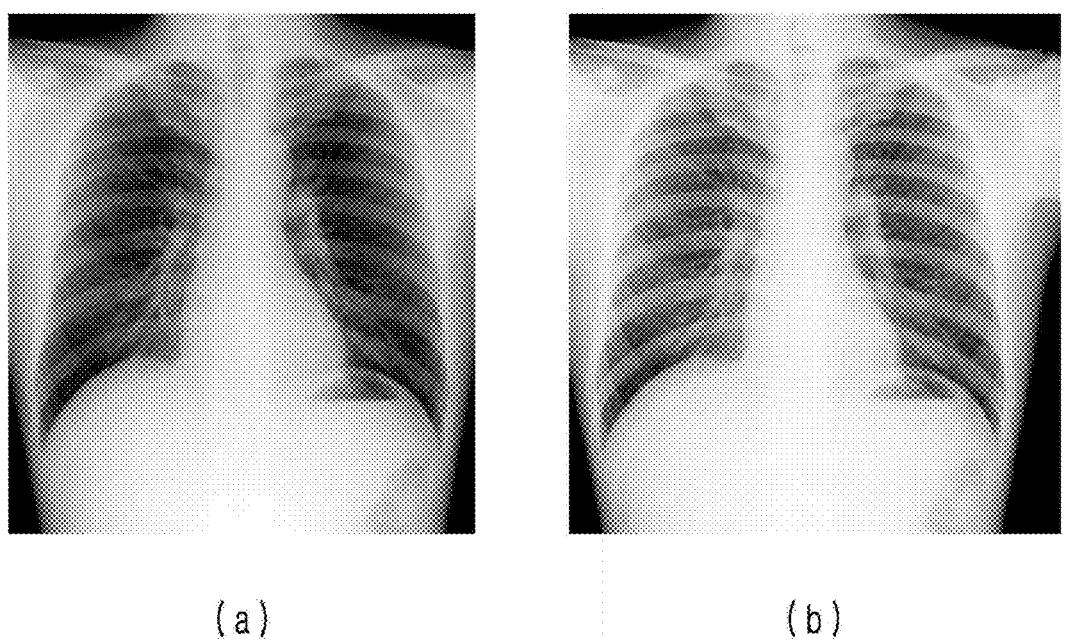
FIG. 5 shows examples of a low-energy image and a high-energy image respectively obtained by a low-energy X-ray and a high-energy X-ray.

FIG. 4 is a graph showing a change in the mass attenuation coefficient depending on the energy of X-rays, and FIG. 5 shows examples of a low-energy image (a) and a high-energy image (b) obtained by low-energy X-ray and high-energy X-ray, respectively. A high-energy image and a low-energy image may be obtained by irradiating high-energy X-ray and low-energy X-ray under the control of the X-ray irradiator 11 and respectively acquiring images.

Figure 6:
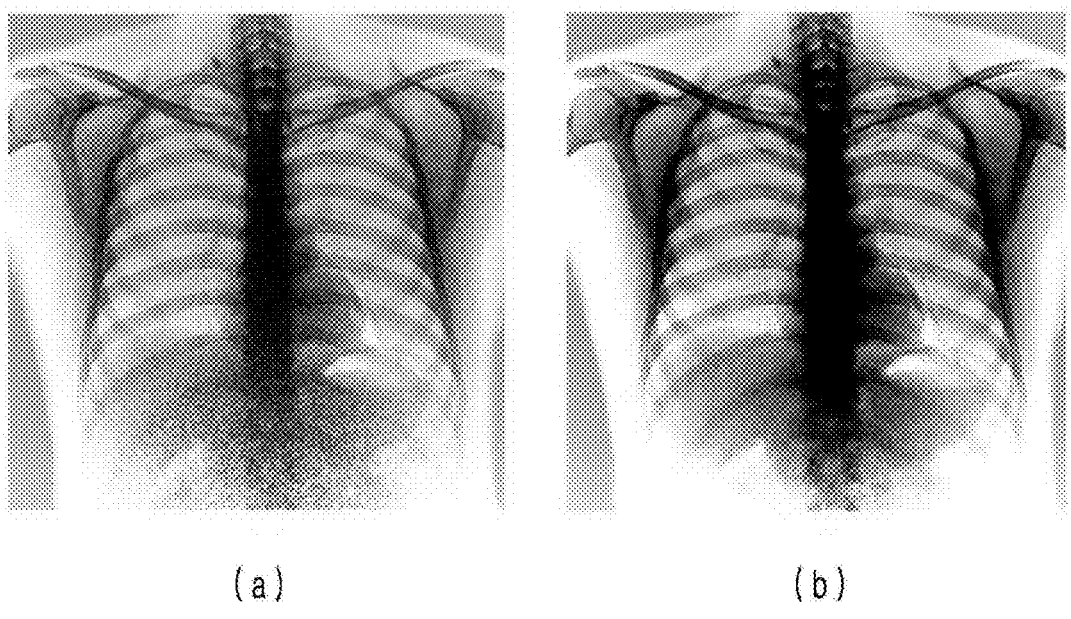
FIG. 6 shows a bone image to which a noise reduction technology using an artificial intelligence is not applied and a bone image to which a noise reduction technology using an artificial intelligence is applied.

Subsequently, a noise reduction is performed on at least one of the acquired high-energy image and the low-energy image, in steps 103 and 104. FIG. 3 exemplarily illustrates a case in which a noise reduction is performed on both a high-energy image and a low-energy image, but a noise reduction may be performed on only one of the high-energy image and the low-energy image. For example, a noise reduction may be achieved by a learning through an artificial intelligence (AI). Specifically, it is possible to reduce noise while minimizing anatomical loss of an image by learning random noise with an artificial intelligence technology using CycleGAN architecture. By applying the noise reduction technology using an artificial intelligence, it is possible to obtain high-quality images even at low doses, thereby improving the accuracy of the determination of factors for the subtraction and an image registration algorithm performed later. FIG. 6 shows a bone image to which a noise reduction technology using an artificial intelligence is not applied (a) and a bone image to which a noise reduction technology using an artificial intelligence is applied (b), respectively. It can be noted that the image quality of the finally obtained subtraction image is improved by applying the noise reduction technology using an artificial intelligence.

Figure 7:
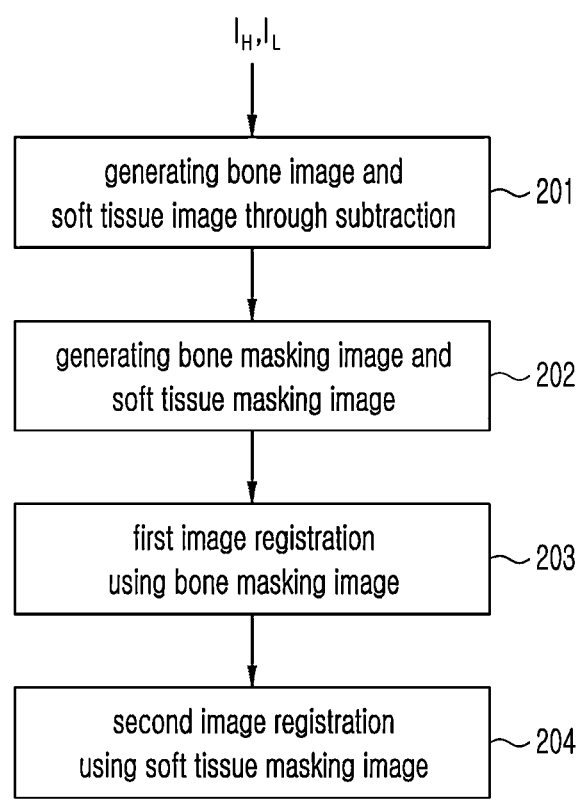
FIG. 7 is a flow chart showing an image registration process according to an embodiment of the present invention.

Subsequently, an image registration is performed on one or more of the high-energy image and the low-energy image in steps 105 and 106. FIG. 3 exemplarily shows a case in which an image registration is performed on both a high-energy image and a low-energy image, but an image registration may be performed only on any one of the high-energy image and the low-energy image. FIG. 7 shows a schematic flowchart of an image registration process according to an embodiment of the present invention.

An image registration is an image processing technique for correcting deformation caused by respiration, heartbeat, etc. that inevitably occurs during imaging in order to compare images of the same patient according to time or point of view. When imaging is performed by irradiating X-rays of different energies twice, a time interval of about 100 to 200 ms inevitably occurs between the two shots, so motion artifact due to movement of the heart and pulmonary blood vessels occurs, resulting in the difficulty in an image registration and the motion artifact deteriorates a material separation performance and an imaging accuracy. In an embodiment of the present invention, in order to reduce the negative influence of the motion artifact, the motion artifact is reduced by applying an image registration algorithm that performs precise correction calculation while preventing an image from being artificially distorted.

In general, a medical image registration uses a non-rigid registration method so that the image is not artificially distorted in consideration of the characteristics of the medical image. Although it is known to use a multi-resolution image processing technique such as a Gaussian or Laplacian pyramid to take into account the differences in the magnitude and direction of motion for respective human tissues, there is a limit to precisely calculate motions for each human tissue with a conventional method in which motions are predicted in a patch unit and corrections are performed. In order to overcome this limitation, in an embodiment of the present invention, the accuracy and calculation speed of the image registration algorithm are improved by applying each algorithm with the division of the motions of the soft tissue and the bone. Since motions of the shoulder, spine and ribs caused by the patient's minute movement or breathing appears globally like the lung area, which is the main interest, whereas the motions of the heart and surrounding pulmonary blood vessels caused by the heartbeat occurs locally and may be opposite to the direction of the motion of the bone, an embodiment of the present invention adopts an image registration algorithm that performs image processing based on the separation of the soft tissue and the bone.

First, referring to FIG. 7, in order to separately apply the image registration algorithm to motions of the bone and soft tissue, a bone image $I_{BONE}$ and a soft tissue image $I_{SOFT}$ are respectively generated by subtracting the high-energy image $I_H$ and the low-energy image $I_L$ in step 201. In order to improve understanding through a brief description, the same reference symbols of $I_H$ and $I_L$ are used for the high-energy image and the low-energy image generated by the digital signal obtained by the X-ray detection modules 12 and 13, the high-energy image and the low-energy image that are obtained by a noise reduction and the high-energy image and the low-energy image that are obtained by the image registration, respectively.

Then, in order to extract position information of the bone and the soft tissue, a bone masking image $I_{BONE\_MASK}$ and a soft tissue masking image $I_{SOFT\_MASK}$ are generated from the generated bone image $I_{BONE}$ and the soft tissue image $I_{SOFT}$, respectively in step 202. The bone masking image $I_{BONE\_MASK}$ may be derived from the bone image $I_{BONE}$ and includes position information of a bone included in the image, specifically, position information of an edge, and the soft tissue masking image $I_{SOFT\_MASK}$ may be derived from the soft tissue image $I_{SOFT}$ and may include position information of the soft tissues included in the image, specifically position information of an edge of the soft tissues.

Figure 8:
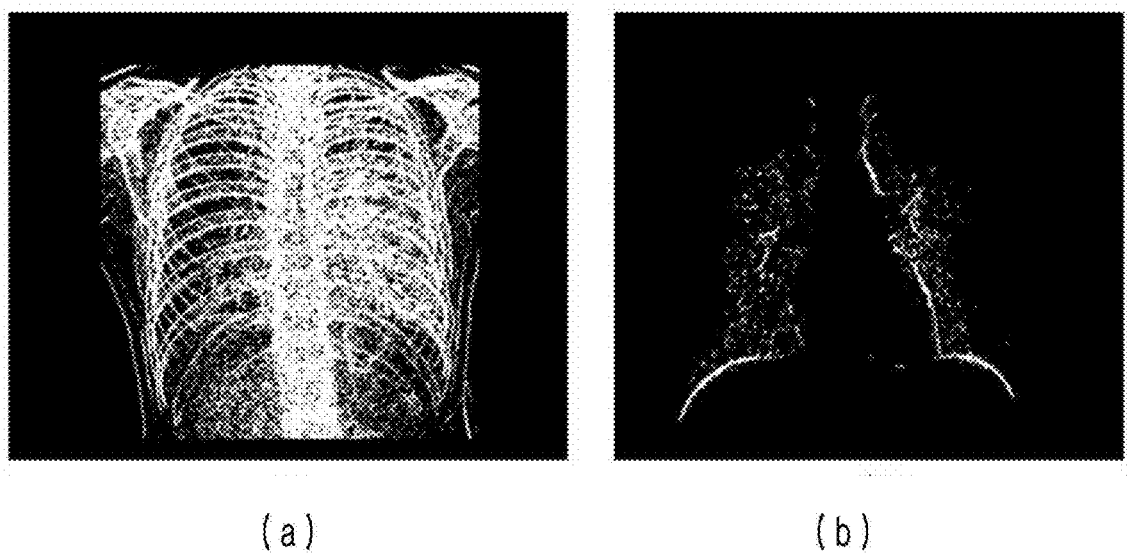
FIG. 8 shows examples of masking images extracted by dividing the position and the motion generation information of bones and soft tissues for image registration according to an embodiment of the present invention.

According to an embodiment of the present invention, in order to apply the image registration algorithms to the motions of bones and soft tissues separately, masking images obtained by extracting each positional information are generated. The principle of subtracting images obtained by high-energy X-ray and low-energy X-ray is used to extract the position information of each tissue, and the position information of respective tissues are extracted from the soft tissue image and the bone image temporarily obtained by subtracting the high-energy image and the low-energy image without being matched. The soft tissue image and the bone image have only information of soft tissue or bone and also include information on the generation of motion noise because they are not matched. Therefore, by extracting edge information from these images, it is possible to obtain a masking image for the position of each bone and soft tissue and the position of the motion of each tissue. FIG. 8 shows masking images extracted by dividing the position and motion generation information of a bone and soft tissue, and (a) is a masking image of the bone and (b) is a masking image of the soft tissue.

Referring back to FIG. 7, a high-energy image $I_H$ and/or a low-energy image $I_L$ are firstly matched in step 203 using the generated bone masking image $I_{BONE\_MASK}$, and then the firstly matched high-energy image $I_H$ and/or low-energy image $I_L$ are secondarily matched in step 204 using the generated soft tissue masking image $I_{SOFT\_MASK}$. The image registration using the bone masking image $I_{BONE\_MASK}$ is an image registration for global optimization, and the image registration using the soft tissue masking image $I_{SOFT\_MASK}$ is an image registration for local optimization.

First, the first image registration using the bone masking image $I_{BONE\_MASK}$ adopts a global optimization technique to prevent motion registration from being matched in conflicting directions over the entire image region and to derive an optimized result with a focus on the bone motion. That is, the first image registration may be performed with a focus on the motion of the bone with Free-Form Deformation (FFD) method, which is an image registration algorithm based on global optimization in order to naturally match the global motion of the human body.

Figure 9:
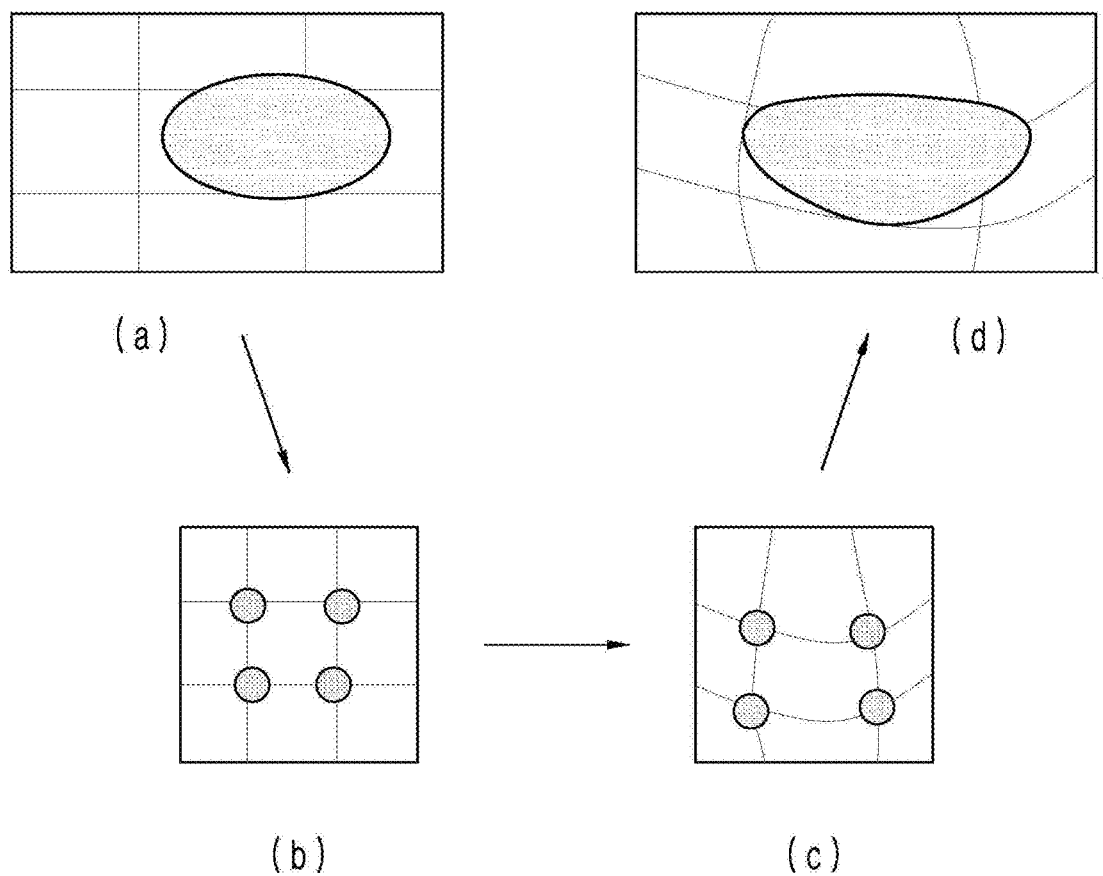
FIG. 9 is a drawing for explaining an image registration using a bone masking image during an image registration process according to an embodiment of the present invention.

FIG. 9 shows an example of registration by image deformation by FFD. In (a) of FIG. 9, the image before deformation is shown, and in (b), the control points of the control grid selected from the image of (a) are shown. The control points shown in (b) of FIG. 9 are changed as shown in (c), and accordingly, the image of (a) may be deformed as shown in (d). This FFD method is a representative image deformation technique, and by manipulating the control points of the control grid, the object can be naturally deformed so as not to violate the laws of physics.

Subsequently, the second image registration using the soft tissue masking image $I_{SOFT\_MASK}$ is performed additionally in a local technique, in consideration of the characteristic that the motion of soft tissues such as the heart and its surrounding pulmonary blood vessels are relatively locally generated, in order to match the motion of the soft tissues to the image obtained by the first registration with a focus of the bone. In particular, since the motion of pulmonary blood vessels can show various directions and sizes independently of the surrounding region unlike the motion of bones, it is difficult to obtain accurate results when applying the FFD technique, in which the surrounding regions are deformed uniformly with the change of the control points. Therefore, in an embodiment of the present invention, the additional registration is performed by a technique of local registration by calculating the similarity between high-energy and low-energy images in a small-sized patch unit including a predetermined number of pixels for a required soft tissue region to locally match. For example, a method such as NCC Normalized Cross Correlation) or MI (Mutual Information) may be used as a method of measuring the similarity, and NCC and MI are methods for measuring similarity by calculating pixel value correlations between two images or calculating information entropy, respectively.

FIG. 10 shows an image obtained by applying an image registration algorithm to an extracted image of a region of interest. FIG. 10 (a) shows an image obtained by applying an image registration in a patch unit according to the conventional method, and FIG. 10 (b) shows an image that is obtained by separating the motions of the bone and the soft tissue having different characteristics and applying image registration algorithms respectively. In the present invention, by distinguishing and matching motions of bones and soft tissues, even if motions generated for bones and the soft tissues conflict with each other, each can be distinguished and precisely matched. If the local registration method is applied to the entire image, it is not natural and there is a problem of the risk of registration noise. Therefore, even if the FFD method based on global optimization with high computational complexity is applied, a registration may be performed by reducing effectively the amount of calculation through a calculation method that focuses on the motion of the bone. In addition, focusing on the fact that the motion of soft tissues such as the heart and surrounding pulmonary blood vessels show a local pattern, only the relevant area is extracted and locally matched to minimize the risk of the generation of noise and thereby matching at a high speed.

Subsequently, referring to FIG. 3, a target image, that is, a standard image 111, a soft tissue image 112 and a bone image 113 are generated through calculation 107 of the high-energy image $I_H$ and the low-energy image $I_L$ that are obtained by the image registration. The standard image 111 may be calculated by summing the high-energy image $I_H$ and the low-energy image $I_L$ and the soft tissue image 112 and the bone image 113 may be calculated by the subtraction of the high-energy image $I_H$ and the low-energy image $I_L$. The conventional standard image may be an image of one energy condition, for example a high-energy image or a low-energy image or may be obtained by simply blending a high-energy image and a low-energy image at a predetermined ratio. The standard image obtained by such a conventional method had a problem in that it does not have good contrast. In contrast, in the present invention, a standard image with effectively improved contrast compared to the conventional standard image can be obtained, and in this sense, the standard image according to the present invention can be referred to as an enhanced standard image.

According to an embodiment of the present invention, a plurality of frequency component images, that is, images for respective frequency bands, are respectively generated by decomposing a high-energy image and a low-energy image, respectively, and merged frequency component images by merging for the respective frequency bands the plurality of generated high-energy frequency component images and the plurality of generated low-energy frequencies, and the standard image is generated using the frequency component images merged for the respective frequency bands. In one embodiment, the high-energy and low-energy frequency component images for each frequency band are generated by generating multi-resolution pyramid images using the high-energy image and the low-energy image. Meanwhile, in another embodiment, the high-energy and low-energy frequency component images for each frequency band are generated through Discrete Wavelet Transform (DWT), and in yet another embodiment, the high-energy and low-energy frequency component images for each frequency band are generated through Discrete Fourier Transform (DFT). Hereinafter, these embodiments will be described in turn.

Figure 11:
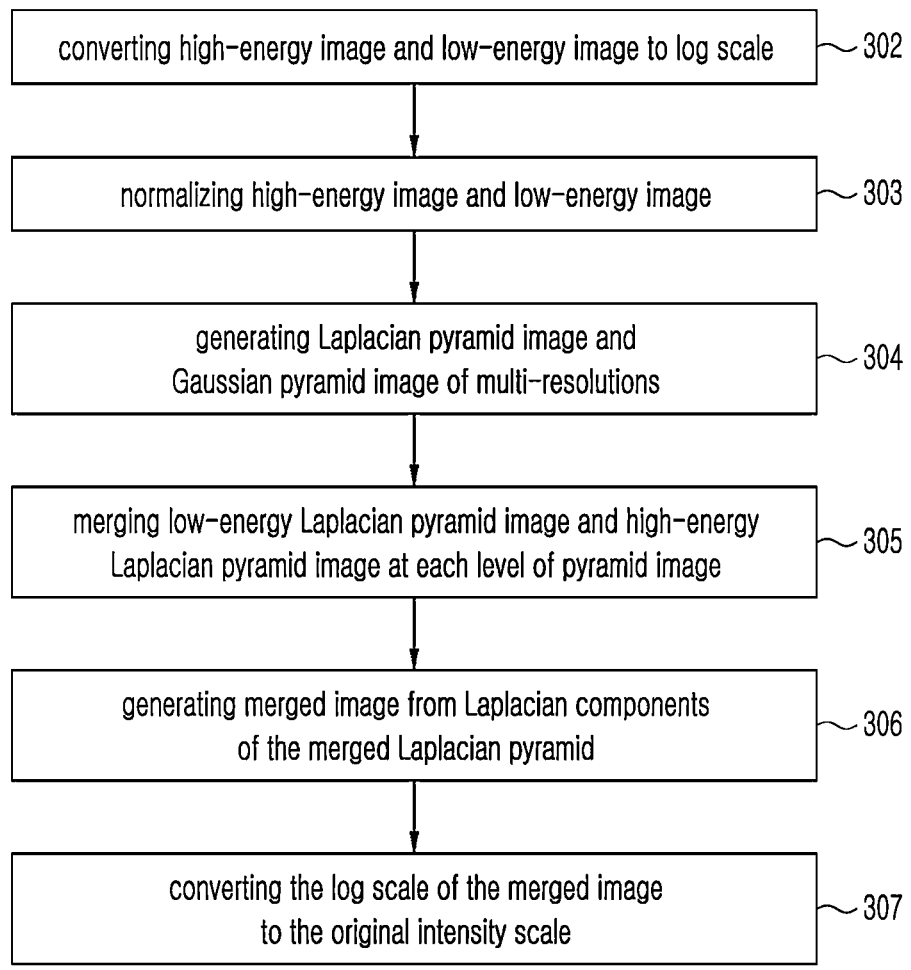
FIG. 11 is flow chart schematically showing a method for generating a standard image according to an embodiment of the present invention.
Figure 12:
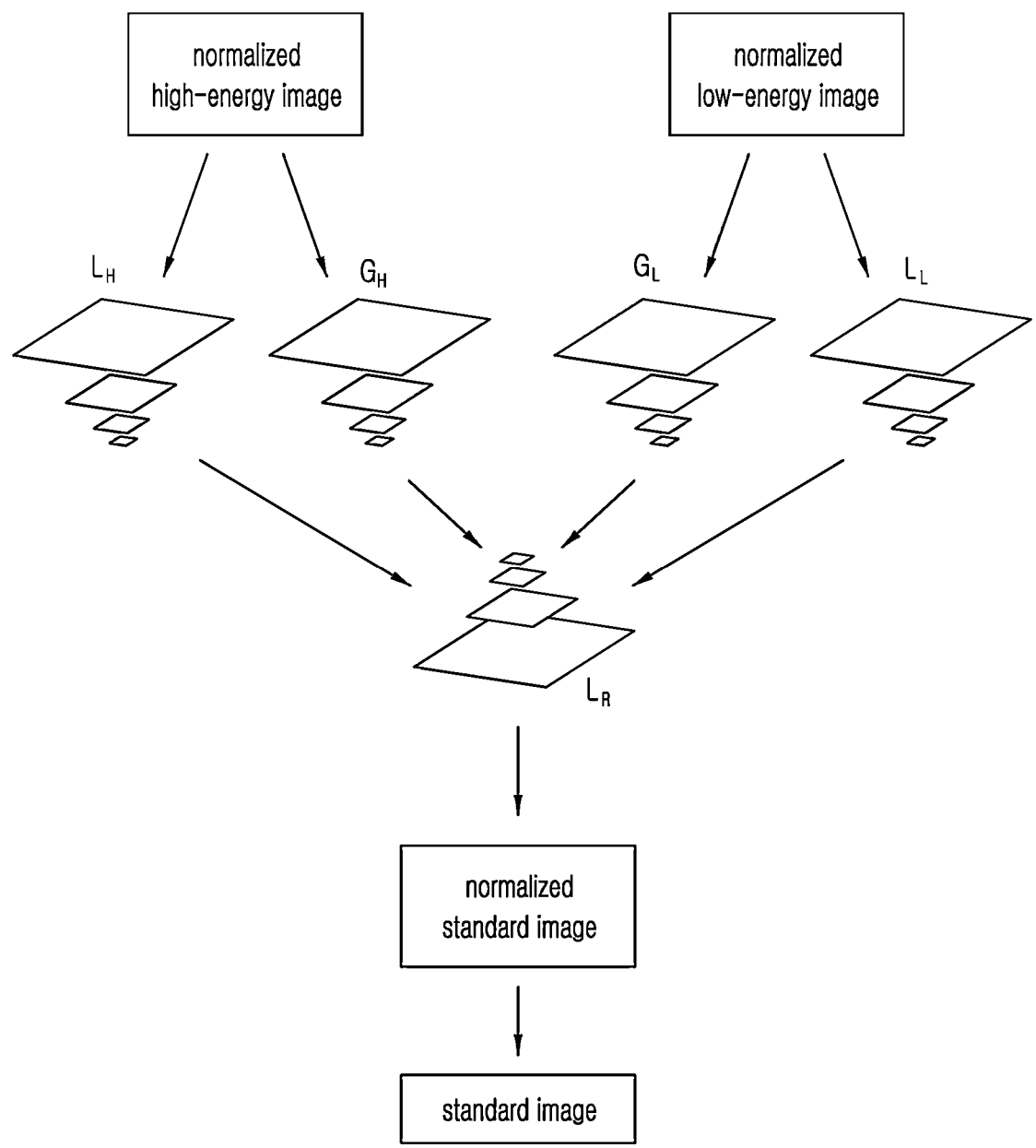
FIG. 12 is a drawing for explaining generation of Laplacian pyramid images and Gaussian pyramid images and generation of an integrated Laplacian pyramid image from an integration of the same, for generating a standard image according to an embodiment of the present invention.

First, a method for generating high-energy and low-energy frequency component images for a plurality of frequency bands through generation of multi-resolution pyramidal images and generating a standard image based thereon will be described with reference to FIGS. 11 to 16. FIG. 11 is a schematic flowchart of a method for generating a standard image 111 according to an embodiment of the present invention, and FIG. 12 schematically shows an image processing process of a method according to an embodiment of the present invention for generating a standard image 111. According to an embodiment of the present invention, the standard image 111 of enhanced good quality with improved global and local contrast by merging the high-energy image $I_H$ and the low-energy image $I_L$ that are obtained by the image registration.

Referring to FIG. 11, as shown in Equation 1 below, the high-energy image $I_H$ and the low-energy image $I_L$ are converted to a logarithmic scale in step 302. This process is performed to generate a linear relationship between the intensity of tissue in the high-energy imaging $I_H$ and the low-energy imaging $I_L$.

$$\hat{I}_L = \ln I_L$$

$$\hat{I}_H = \ln I_H \qquad \text{[Equation 1]}$$

where $\hat{I}_L$ and $\hat{I}_H$ are the low-energy image and the high-energy image that are converted to logarithmic scale.

Next, for a comparison operation between the intensities of the high-energy image $I_H$ and the low-energy image $I_L$, the high-energy image $I_H$ and the low-energy image $I_L$ are normalized in step 303. For example, image standardization as shown in Equation 2 below may be selected as a method for normalization.

$$\bar{I}_L = \frac{\hat{I}_L - \mu_L}{\sigma_L} \qquad \text{[Equation 2]}$$

$$\bar{I}_H = \frac{\hat{I}_H - \mu_H}{\sigma_H}$$

Where $\bar{I}_L$ and $\bar{I}_H$ are the normalized low-energy and high-energy images, $\mu_L$ and $\mu H$ are the averages of $\hat{I}_L$ and $\hat{I}_H$, and $\sigma_L$ and $\sigma_H$ are the standard deviations of $\hat{I}_L$ and $\hat{I}_H$.

Subsequently, multi-resolution pyramid images, that is, high-energy and low-energy frequency component images for each frequency band, are generated using the normalized low-energy image and the normalized high-energy image in step 304. The generated pyramid images of different resolutions represent frequency components for each frequency band. By decomposing the image for each frequency band, it is possible to remove the noise component of the high frequency band, thereby increasing the accuracy of the algorithm.

When a multi-resolution image is generated using the normalized low-energy image and the normalized high-energy image, the generated pyramid images of different resolutions represent frequency component images for each frequency band. When the multi-resolution pyramid images are generated and the image is decomposed for each frequency band, the noise component of the high frequency band can be removed and thus the accuracy of the algorithm can be increased. In addition, the highest-level Gaussian pyramid component, that is, the image of the low frequency band, shows global contrast, and as it goes up to the high frequency band, it shows edge information of minute part such as pulmonary blood or the like from edge information of thick edge information of parts such as bone and heart.

Referring to FIG. 12, a high-energy Laplacian image pyramid $L_H$ and a high-energy Gaussian image pyramid $G_H$ are generated from the normalized high-energy image, and a low-energy Laplacian image pyramid $L_L$ and a low-energy Gaussian image pyramid are generated from the normalized low-energy image $G_L$ are generated from the normalized low-energy image. It is configured such that as the level of the pyramid increases, the resolution of the corresponding image decreases. For example, if a pyramid image consists of four levels, the pyramid image of the lowest level may have a resolution of 10001000, the pyramid image of the next level may have a resolution of 500*500, and the pyramid image of the next level may have a resolution of 250*250, and the highest level pyramid image may have a resolution of 125*125. In this way, a plurality of images of a pyramid structure having multi-resolution can be implemented.

Specifically, Gaussian and Laplacian pyramid images may be generated as shown in Equation 3 below.

$$G_L^0 = \bar{I}_L; \quad G_H^0 = \bar{I}_H$$

$$G_L^i = g*DG_L^{i-1}; \quad H_H^i = g*DG_H^{i-1}, \quad i=1, 2, \ldots, n$$

$$L_L^n = G_L^n; \quad L_H^n = G_H^n$$

$$L_L^i = G_L^i - UG_L^{i+1}; \quad L_H^i = G_H^i - UG_H^{i+1}, \quad i=1, 2, \ldots, n-1 \quad \text{[Equation 3]}$$

where $G_L^k$, $H_H^k$, $L_L^k$, $L_H^k$ are Gaussian and Laplacian pyramid images of k-th level of the normalized low-energy and high-energy images, D and U are a down-sampling operator and an up-sampling operator respectively, * is a convolution operator, and g is a Gaussian kernel.

Figure 13:
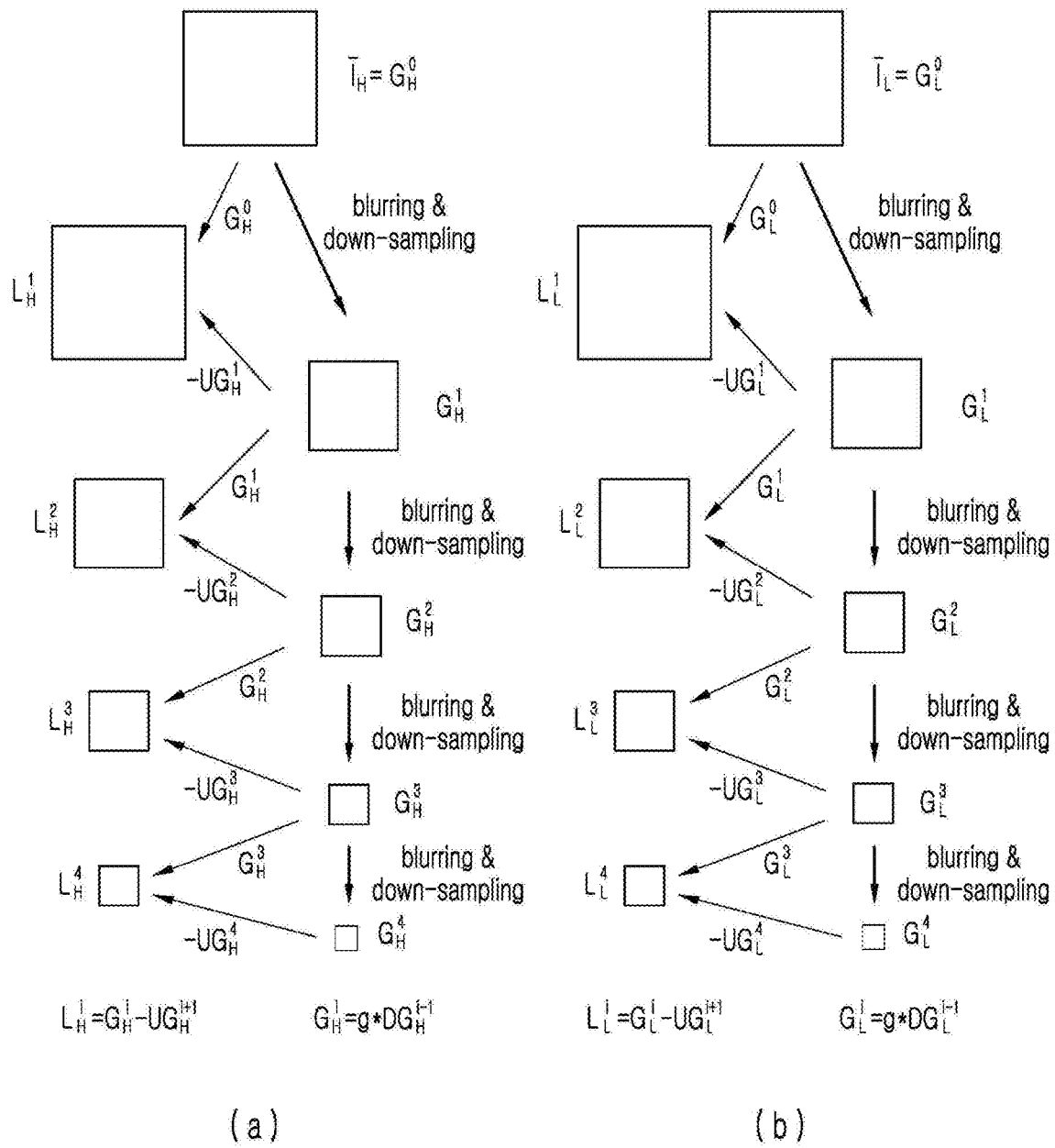
FIG. 13 is a drawing for explaining the process of generating Gaussian pyramid images and Laplacian pyramid images according to an embodiment of the present invention.

In FIG. 13, an image processing process (a) for generating a high-energy Gaussian pyramid image $G_H$ and a high-energy Laplacian pyramid image $L_H$ from the normalized high-energy image $\bar{I}_H$ and a image processing process (b) for generating a low-energy Gaussian pyramid image $G_L$ and a low-energy Laplacian pyramid image $L_L$ from the normalized low-energy image $\bar{I}_L$ are shown. The normalized high-energy image $\bar{I}_H$ is set as the lowest level Gaussian pyramid image $G_H^0$, and the next level of the Gaussian pyramid image $G_H^1$, $G_H^2$, $G_H^3$, $G_H^4$ are sequentially generated by blurring and down-sampling it in turn. In this case, blurring and down-sampling may be performed using the above-described convolution operator and a Gaussian kernel. In this case, as the level increases by down-sampling, the size (i.e., resolution) of the image may be sequentially reduced to ¼. The Laplacian pyramid image $L_H$ may be sequentially calculated using the Gaussian pyramid image. That is, the Laplacian pyramid image $L_H^1$ of the lowest level may be calculated by subtracting the up-sampled image of the Gaussian pyramid image $G_H^1$ of the next level from the lowest Gaussian pyramid image $G_H^0$. In the same manner, Laplacian pyramid images $L_H^2$, $L_H^3$, $L_H^4$ of the following levels may be sequentially calculated. In addition, in the same manner, low-energy Gaussian pyramid images $G_L^0$, $G_L^1$, $G_L^2$, $G_L^3$, $G_L^4$ and low-energy Laplacian pyramid images $L_L^1$, $L_L^2$, $L_L^3$, $L_L^4$ may be sequentially calculated from the normalized low-energy image $\bar{I}_L$. At this time, the lowest Laplacian pyramid image corresponds to noise, the Laplacian pyramid image of the next level mainly contains information about edges of the blood vessel, and the Laplacian pyramid image of the next level mainly contains information about the bone structure, and the highest-level Laplacian pyramid image mainly contains information about the overall contrast of major tissues such as bones and lungs.

Next, referring again to FIG. 11, the high-energy Laplacian pyramid image $L_H$ and the low-energy Laplacian pyramid image $L_L$ are merged at each level of the pyramid in step 305. In this merging step, the components at each level are selected so that the global and local contrasts can be increased. Referring to FIG. 12, a high-energy Laplacian pyramidal image $L_H$ and a low-energy Laplacian pyramidal image $L_L$ are merged at each level to generate a merged Laplacian pyramidal image $L_R$ including images of a plurality of levels.

Figure 14:
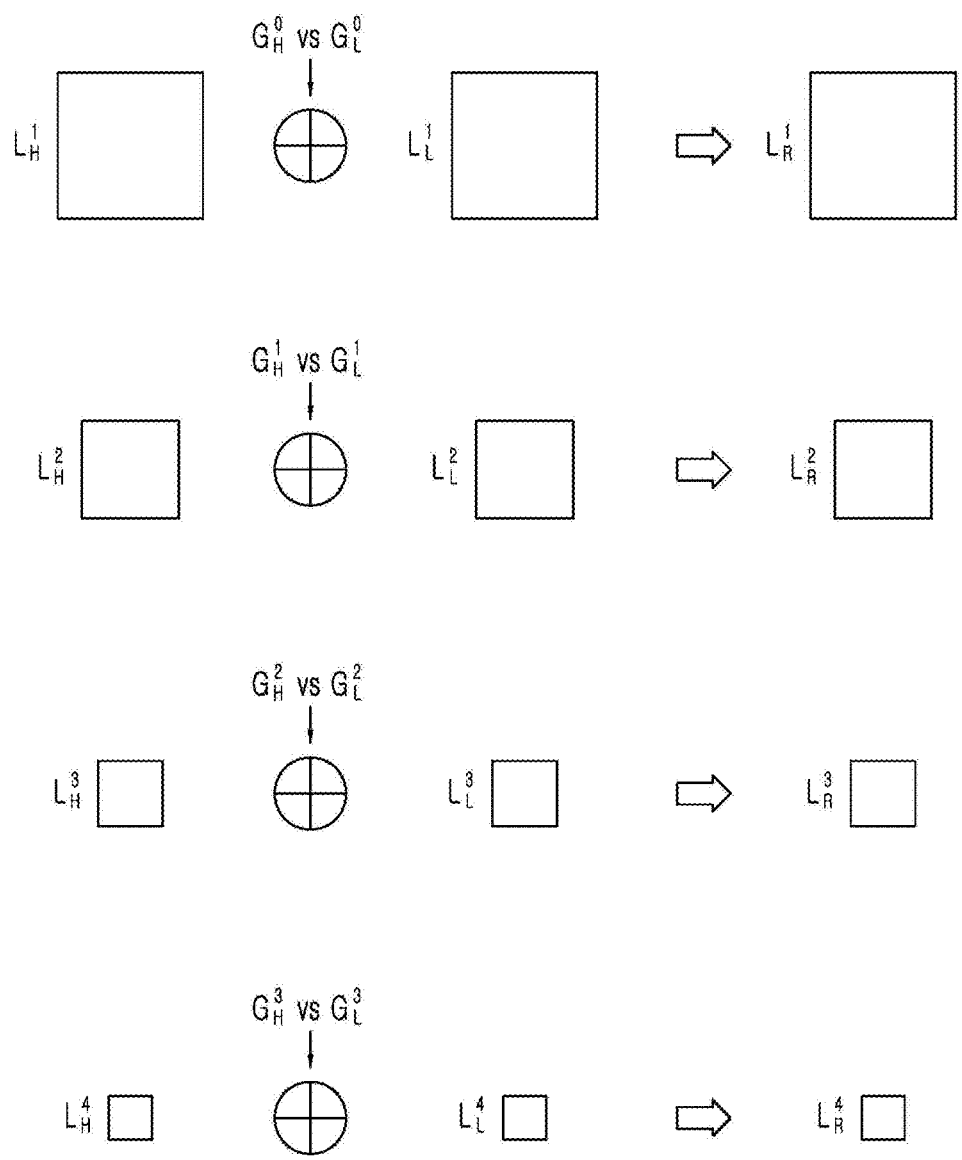
FIG. 14 is a drawing for explaining the process of integrating high-energy Laplacian images and low-energy Laplacian images according to an embodiment of the present invention.

FIG. 14 and FIG. 15 schematically show an image processing process for merging a high-energy Laplacian pyramidal image $L_H$ and a low-energy Laplacian pyramidal image $L_L$. Referring to FIG. 14, respective components $L_R^1$, $L_R^2$, $L_R^3$, $L_R^4$ of the merged Laplacian pyramid image $L_R$ are generated by respectively merging the components $L_H^1$, $L_H^2$, $L_H^3$, $L_H^4$ of each level of the high-energy Laplacian pyramid image LH and the components $L_L^1$, $L_L^2$, $L_L^3$, $L_L^4$ of the same level of the low-energy Laplacian pyramid image LL.

In an embodiment of the present invention, when merging the low-energy Laplacian pyramidal image and the high-energy Laplacian image of each level, for a pixel or for a pixel patch, i.e., a group of pixels of a predetermined number, a pixel or a pixel patch of one of the high-energy Laplacian pyramid image $L_H$ and the low-energy Laplacian pyramid image $L_L$ may be selected to be merged. At this time, whether to select the corresponding pixel or patch of the high-energy Laplacian pyramid image $L_H$ or the low-energy Laplacian pyramid image $L_L$ of the same level may be performed based on comparison of statistical values indicating contrasts of corresponding pixel patches of the high-energy Gaussian pyramid image $G_H$ and the low-energy Gaussian pyramid image $G_L$ of the same level. At this time, the corresponding pixel patch of the Gaussian pyramid image may be a pixel patch including pixels surrounding a pixel corresponding to a pixel of the Laplacian pyramid image or the same pixel patch with the Laplacian pyramid image. For example, with respect to which of the corresponding pixels or patches of the low-energy and high-energy Laplacian pyramid images to be selected, a pixel or a pixel patch of both Laplacian pyramid images corresponding to one that has a statistical value, i.e., a standard deviation of contrasts of the pixels included in the pixel patch or an average of the absolute deviation, indicating greater contrast for the corresponding pixel or pixel patch of the high-energy Gaussian pyramid $G_H$ and the low-energy Gaussian pyramid image $G_L$ is selected.

FIG. 15 shows an example of merging the lowest-level high-energy Laplacian pyramid image $L_H^1$ and the low-energy Laplacian pyramid image $L_L^1$ according to the comparison result between the lowest-level high-energy Gaussian pyramid image $G_H^0$ and the low-energy Gaussian pyramid image $G_L^0$. Here, the Gaussian pyramid image $G_H^0$, $G_L^0$ and the Laplacian pyramid image $L_H^1$, $L_L^1$ are pyramid images of the same level, that is, images having the same resolution. First, referring to (a) of FIG. 15, in relation to which one of the first patches of the high-energy Laplacian pyramid image $L_H^1$ and the low-energy Laplacian pyramid image $L_L^1$ is selected, the one having greater statistical value, for example standard deviation ($STD_{H\_11}$, $STD_{L\_11}$) of the pixels included in the pixel, indicating contrasts of the same patch of the high-energy Gaussian pyramid image $G_H^0$ and the low-energy Gaussian pyramid image $G_L^0$, that is, the high-energy side is selected, and accordingly the brightness value $I_{H\_11}$ of the corresponding patch of the high-energy Laplacian pyramid image $L_H^1$ is selected as a brightness value of the corresponding patch of the lowest level image $L_R^1$ of the merged Laplacian pyramid image $L_R$. Next, FIG. 15 (b) shows an example of selecting the brightness value of the second patch of the lowest level image $L_R^1$ of the merged Laplacian pyramid image $L_R$. As in FIG. 15 (a), the side having greater standard deviation ($STD_{H\_12}$, $STD_{L\_12}$) of the brightness of the pixels belonging to the corresponding patch of the high-energy Gaussian pyramid image $G_H^0$ and the low-energy Gaussian pyramid image $G_L^0$ is selected, that is, the low-energy side is selected, and accordingly the brightness value $I_{L\_12}$ of the corresponding patch of the low-energy Laplacian image $L_L^1$ is selected as the brightness value of the corresponding patch of the merged Laplacian pyramid image $L_R$.

The higher level pixel contrast values of the pyramid represent global contrast and the lower level pixel contrast values of the pyramid represent local contrast. In this way, the Laplacian components at each pyramid level can be determined.

Meanwhile, in another embodiment of the present invention, the merging of the high-energy Laplacian pyramid image $L_H$ and the low-energy Laplacian pyramid image $L_L$ is performed by selecting the side that has a greater statistical value indicating the contrast of the corresponding patch of the high-energy Laplacian pyramid image and the low-energy Laplacian pyramid image, e.g., a greater average or median of the brightness of the pixels belonging to the patch, instead of being based on the comparison of the statistical values indicating the contrasts of the corresponding patch of the high-energy Gaussian pyramid image and the low-energy Gaussian pyramid image.

Next, referring again to FIG. 11, a merged image is generated from Laplacian components of the merged Laplacian pyramid obtained by merging the high-energy Laplacian image and the low-energy Laplacian image in step 306. Here, a merged image may be generated by sequentially merging the Laplacian components from the highest level.

Figure 16:
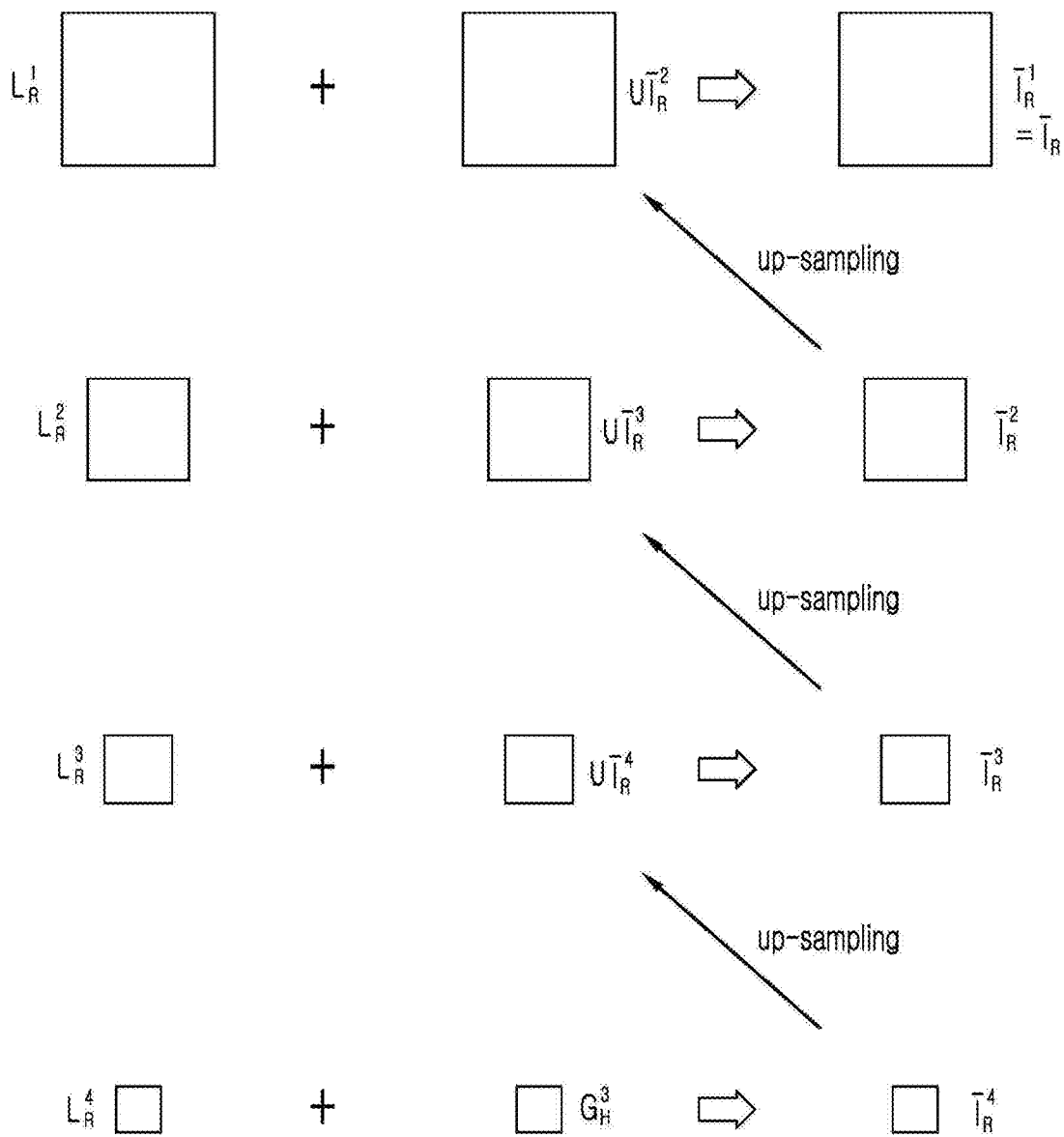
FIG. 16 is a drawing for explaining a method for generating integrated frequency component images according to an embodiment of the present invention.

FIG. 16 shows an example of generating a merged image by reconstructing a merged Laplacian pyramid image. For example, referring to FIG. 16, a first-order merged image component $\bar{I}_R^4$ is generated by summing the highest-level image $L_R^4$ of the merged Laplacian pyramid and a high-energy Gaussian image $G_H^3$ of the same resolution. Here, summing the images may mean adding the brightness values of pixels of the two images to be merged. Then, an image $U\bar{I}_R^4$ obtained by up-sampling the first merged image component $\bar{I}_R^4$ and the next-level merged Laplacian pyramid image $L_R^3$ are summed to generate a second merged image component $\bar{I}_R^3$. Then, an image $U\bar{I}_R^3$ obtained by up-sampling the second merged image component $\bar{I}_R^3$ and the merged Laplacian pyramid image of the next level $L_R^2$ are summed to generate a third merged image component $\bar{I}_R^2$. Then, an image $U\bar{I}_R^2$ obtained by up-sampling the third merged image component $\bar{I}_R^2$ and the merged Laplacian pyramid image of the next level $L_R^1$ are summed to generate a fourth merged image component $\bar{I}_R^1$. In this case, the generated fourth merged image component $\bar{I}_R^1$ is a normalized merged image, that is, a normalized standard image $\bar{I}_R^1$.

Merged Laplacian pyramid images are sequentially obtained from the highest level to the lowest level of the pyramid (sequentially from the bottom to the top in FIG. 16). Since the higher level pyramid images well represent global image components and the lower level pyramid images well represent local image components, sequential merging from the highest level of the pyramid to the lower level to focus on the global image components first and then to gradually focus on the local image components.

Next, referring again to FIG. 11, a scale transformation is performed to return the log scale of the merged image to the original intensity scale in step 307. Thereby, a standard image is generated.

Hereinafter, a method of generating a standard image using a discrete wavelet transform (DWT) will be described with reference to FIG. 17 to FIG. 19.

By decomposing the normalized low-energy image and high-energy image with discrete wavelet transform (DWT), frequency component images for each frequency band may be generated. Discrete wavelet transform is a method to improve the conversion efficiency by decomposing an image into different frequency components according to human visual characteristics using a localized basis and obtaining and processing each component related to the resolution corresponding to each frequency band.

The DWT can be expressed with the following Equation 4.

$$W'(j,k) = <x(t), \psi_{j,k}(t)> = \frac{1}{\sqrt{2^j}} \int x(t)\psi^*\left(\frac{t-k2^j}{2^j}\right)dt \quad \text{[Equation 4]}$$

where x(t) is an original image signal, $\psi$ is a wavelet function, $2^j$ is a compression coefficient for determining the magnitude, $k2^j$ is a transition coefficient related to the movement along the time axis and uses a mother wavelet function whose magnitude changes depending on the scale.

Figure 17:
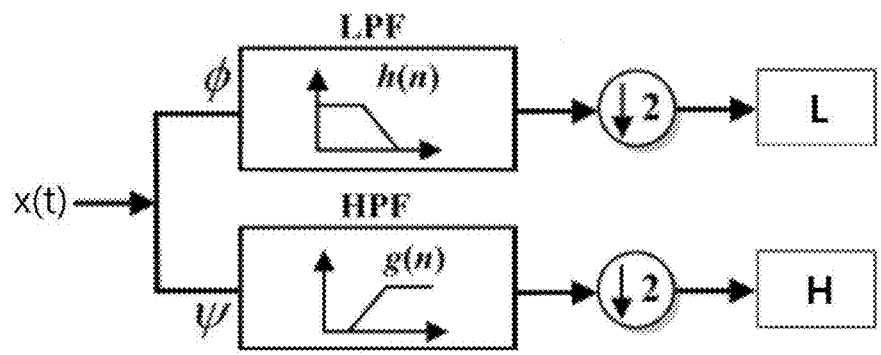
FIG. 17 shows a filtering process of a discrete wavelet transform according to an embodiment of the present invention.

Referring to FIG. 17, the original discrete signal is decomposed into several subband signals having different frequencies through down-sampling of the multi-resolution analysis and is synthesized into the original discrete signal through up-sampling. The original image signal is decomposed into a low-pass component L and a high-pass component H using a low-pass filter (LPF, h(n)) and a high-pass filter (HPF, g(n)). In this case, the used scale function $\phi(t)$ may be as in Equation 5 below, and the wavelet function $\psi(t)$ may be as in Equation 6 below.

$$\phi(t) = \sqrt{2}\Sigma_k h(k)\phi(2t-k) \quad \text{[Equation 5]}$$

$$\psi(t) = \sqrt{2}\Sigma_k g(k)\phi(2t-k) \quad \text{[Equation 6]}$$

Since wavelet transform can interpret spatial information and frequency information in each subband, it enables adaptive image processing such as reduction of specific high-frequency components corresponding to noise or preservation of specific edge information.

Figure 18:
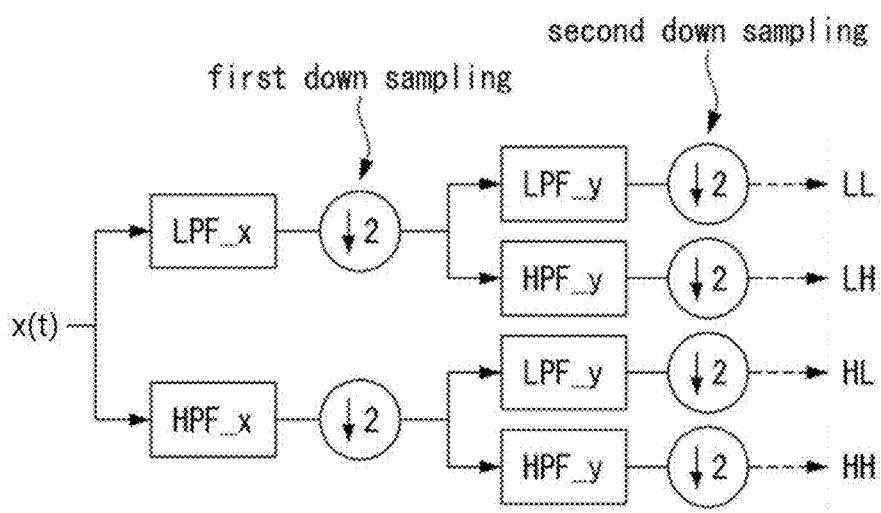
FIG. 18 is a drawing for explaining a process of generating subband component images by a discrete wavelet transform according to an embodiment of the present invention.

Referring to FIG. 18, a transformed image obtained by performing discrete wavelet transform on an original image may include four subband component images LL, LH, HL, and HH. The LL subband component image may consist of coefficients in which the high frequency components in the image is excluded by applying a horizontal low pass filter LPF_y and a vertical low pass filter LPF_x to the original image x, and the HH subband component only represent the high frequency components by applying a horizontal high-pass filter HPF_y and a vertical high-pass filter HPF_x to the original image x, as opposed to the LL subband component image. In addition, the LH subband component image is obtained by applying a horizontal high-pass filter HPF_y to the original image x and includes an error component in the horizontal direction frequency. The HL subband component image is obtained by applying a vertical high frequency filter HPF_x to the original image x and includes a vertical frequency error component. Here, after applying the high-frequency or low-pass filter, first down-sampling and second down-sampling may be performed, respectively.

Next, when merging the low-energy component image and the high-energy component image for each frequency band in each step, similarly to the above-described embodiment, a pixel or a pixel patch of one of the high-energy component and the low-energy component for each pixel of the image may be selected to be merged. In this case, when merging is performed based on the comparison of statistical values of the corresponding patches of the high-energy frequency component image and the low-energy frequency component image, the statistical value representing the contrast may be the average value or median value of the absolute values of a plurality of pixel values constituting the corresponding patch.

According to another embodiment of the present invention, a high-frequency component image and a low-frequency component image for each frequency band may be generated by applying a discrete Fourier transform (DFT). The discrete Fourier transform can be expressed by Equation 7 below.

$$X_k = \Sigma x_n e^{-2\pi i k n/N} \quad \text{[Equation 7]}$$

where x is the original image signal, and k is 0, 1, 2, ... N−1.

The inverse transform can be expressed by the following Equation 8.

$$x_n = \frac{1}{N} \sum X_k e^{2\pi i k n/N} \quad \text{[Equation 8]}$$

where x is the original image signal, and k is 0, 1, 2, ... N−1.

Referring back to FIG. 3, a soft tissue image 112 and a bone image 113 is generated through the calculation 107 of the high-energy image $I_H$ and the low-energy image $I_L$ that are image-registered. The soft tissue image 112 and the bone image 113 may be obtained through a subtraction calculation of the low-energy image from the high=energy image by applying a subtraction factor. Acquiring the soft tissue image and the bone image through the subtraction of the high-energy image and the low-energy image may be performed by a known method.

Although preferred embodiments of the present invention have been described in detail above, the scope of the present invention is not limited thereto, and various modifications and improvements by those skilled in the art using the basic concept of the present invention as defined in the following claims are also within the scope of the invention.

What is claimed is:

1. An X-ray imaging device comprising:
an X-ray irradiation module configured to irradiate X-ray;
an X-ray detection module configured to detect X-ray passed through an object after being irradiated from the X-ray irradiation module to output a corresponding digital signal; and
an image processor configured to generate an X-ray image using an output signal of the X-ray detection module, wherein the image processor is configured to perform:
acquiring a high-energy image and a low-energy image respectively obtained by X-ray of relatively high-energy and X-ray of relatively low-energy;
generating high-energy frequency component images for each of a plurality of frequency bands by decomposing the high-energy image;
generating low-energy frequency component images for each of a plurality of frequency bands by decomposing the low-energy image;
generating merged frequency component images by merging at least a portion of the high-energy frequency component images for each of the plurality of frequency bands and at least a portion of the low-energy frequency component images for each of the plurality of frequency bands; and
generating a standard image using the merged frequency component images,
wherein the high-energy frequency component images for the plurality of frequency bands comprise high-energy Laplacian pyramid images of a plurality of frequency band levels and high-energy Gaussian pyramid images of a plurality of frequency band levels,
wherein the low-energy frequency component images for the plurality of frequency bands comprise low-energy Laplacian pyramid images of a plurality of frequency band levels and low-energy Gaussian pyramid images of a plurality of frequency band levels,
wherein the merged frequency component images are generated by merging the high-energy Laplacian pyramid images and the low-energy Laplacian pyramid images for each frequency band level,
wherein the high-energy Laplacian pyramid images and the low-energy Laplacian pyramid images are merged with each other for a pixel for each level or for a patch having a plurality of pixels, and
wherein when the high-energy Laplacian pyramid images and the low-energy Laplacian pyramid images are merged for each level, the merging is performed by selecting a pixel or a patch of one of the high-energy Gaussian pyramid images and the low-energy Gaussian pyramid images of a corresponding level that has a statistical value indicating a higher contrast, or a pixel or a patch of one of the high-energy Laplacian pyramid image and the low-energy Laplacian pyramid image that has a statistical value indicating a higher contrast.

2. The X-ray imaging device of claim 1, wherein when the merging is performed based on a comparison of statistical values of corresponding patches of the high-energy Gaussian pyramid images and the low-energy Gaussian pyramid images, the statistical value indicating the contrast is a standard deviation or an average of absolute deviations of brightness values of the plurality of pixels constituting a corresponding patch, and
wherein when the merging is performed based on a comparison of statistical values of corresponding patches of the high-energy Laplacian pyramid images and the low-energy Laplacian pyramid images, the statistical value indicating the contrast is a standard deviation or an average of absolute deviations of brightness values of the plurality of pixels constituting a corresponding patch.

3. An X-ray imaging device comprising:
an X-ray irradiation module configured to irradiate X-ray;
an X-ray detection module configured to detect X-ray passed through an object after being irradiated from the X-ray irradiation module to output a corresponding digital signal; and
an image processor configured to generate an X-ray image using an output signal of the X-ray detection module,
wherein the image processor is configured to perform:
acquiring a high-energy image and a low-energy image respectively obtained by X-ray of relatively high-energy and X-ray of relatively low-energy;
generating high-energy frequency component images for each of a plurality of frequency bands by decomposing the high-energy image;

generating low-energy frequency component images for each of a plurality of frequency bands by decomposing the low-energy image;

generating merged frequency component images by merging at least a portion of the high-energy frequency component images for each of the plurality of frequency bands and at least a portion of the low-energy frequency component images for each of the plurality of frequency bands; and generating a standard image using the merged frequency component images, wherein the high-energy frequency component images for each of the plurality of frequency bands comprise high-energy frequency component images for each of the plurality of frequency bands decomposed by a Fourier transform or a wavelet transform, wherein the low-energy frequency component images for each of the plurality of frequency bands comprise a plurality of low-energy frequency component images for each of the plurality of frequency bands decomposed by a Fourier transform or a wavelet transform, and wherein the merged frequency component images are generated by the merging of the high-energy frequency component images and the low-energy frequency component images for each frequency band and an inverse Fourier transform or an inverse wavelet transform thereof, wherein the high-energy frequency component images and the low-energy frequency component images are merged with each other for a pixel or for a patch having a plurality of pixels, and wherein when the high-energy frequency component images and the low-energy frequency component images are merged for each frequency band, the merging is performed by selecting a pixel or a patch of one of the high-energy frequency component images and the low-energy frequency component images of a corresponding frequency band that has a statistical value indicating a greater contrast to be merged.

4. The X-ray imaging device of claim 3, wherein when the merging is performed based on a comparison of statistical values of corresponding patches of the high-energy frequency component images and the low-energy frequency component images, the statistical values representing the contrast is an average or a median of absolute values of a plurality of pixel values constituting a corresponding patch.

5. The X-ray imaging device of claim 1, wherein the standard image is generated by merging frequency component images for a plurality of frequency bands constituting the merged frequency component images.

6. The X-ray imaging device of claim 1, wherein the image processor is configured to further perform a step of performing an image registration at least one of the high-energy image and the low-energy image, and wherein the image registration comprises a plurality of image registrations that are performed respectively using bone masking information and soft tissue masking information to reflect a difference of motions of a bone and soft tissues.

7. The X-ray imaging device of claim 6, wherein the performing an image registration comprises:

generating a bone image and a soft tissue image by subtraction of the high-energy image and the low-energy image, respectively;

generating a bone masking image including the bone masking information and a soft tissue masking image from the generated bone image and the generated soft tissue image, respectively;

firstly registering at least one of the high-energy image and the low-energy image to be registered using the bone masking image, and additionally registering at least one of the firstly registered high-energy image and the low-energy image using the soft tissue masking image.

8. The X-ray imaging device of claim 7, wherein the bone masking image comprises edge position information of a bone contained in the bone image, and wherein the soft tissue masking image comprises edge position information of a soft tissue contained in the soft tissue image.

9. The X-ray imaging device of claim 7, wherein the firstly registering using the bone masking image uses a global optimization-based image registration algorithm.

10. The X-ray imaging device of claim 9, wherein the image registration algorithm is an image registration algorithm that focuses on motion of a bone in a Free-Form Deformation (FFD) method.

11. The X-ray imaging device of claim 7, wherein the additionally registering using the soft tissue masking image is performed by locally registering by measuring a similarity of the high-energy image and the low-energy image in a patch including a predetermined number of pixels.

12. The X-ray imaging device of claim 11, wherein the similarity is measured through pixel values or information entropy between the high-energy image and the low-energy image.

13. The X-ray imaging device of claim 12, wherein the similarity is measured using at least one of NCC (Normalized Cross Correlation) and MI (Mutual Information).

14. An X-ray imaging method comprising:

irradiating X-ray to an object to be imaged;

detecting X-ray passed through the object and generating a corresponding digital signal; and generating an X-ray image using the digital signal, wherein the generating an X-ray image comprises:

acquiring a high-energy image and a low-energy image respectively obtained by X-ray of relatively high-energy and X-ray of relatively low-energy;

generating high-energy frequency component images for each of a plurality of frequency bands by decomposing the high-energy image;

generating low-energy frequency component images for each of a plurality of frequency bands by decomposing the low-energy image;

generating merged frequency component images by merging at least a portion of the high-energy frequency component images for each of the plurality of frequency bands and at least a portion of the low-energy frequency component images for each of the plurality of frequency bands, and generating a standard image using the merged frequency component images, wherein the high-energy frequency component images for the plurality of frequency bands comprises high-energy Laplacian pyramid images of a plurality of frequency band levels and high-energy Gaussian pyramid images of a plurality of frequency band levels, wherein the low-energy frequency component images for the plurality of frequency bands comprises low-energy Laplacian pyramid images of a plurality of frequency band levels and low-energy Gaussian pyramid images of a plurality of frequency band levels, wherein the merged frequency component images are generated by merging the high-energy Laplacian pyramid images and the low-energy Laplacian pyramid images for each frequency band level, wherein the high-energy Laplacian pyramid images and the low-energy Laplacian pyramid images are merged with each other for a pixel for each level or for a patch having a plurality of pixels, and wherein when the high-energy Laplacian pyramid images and the low-energy Laplacian pyramid images are merged for each level, the merging is performed by selecting a pixel or a patch of one of the high-energy Gaussian pyramid images and the low-energy Gaussian pyramid images of a corresponding level that has a statistical value indicating a higher contrast, or a pixel or a patch of one of the high-energy Laplacian pyramid images and the low-energy Laplacian pyramid images that has a statistical value indicating a higher contrast.

15. An X-ray imaging method comprising:

irradiating X-ray to an object to be imaged;

detecting X-ray passed through the object and generating a corresponding digital signal; and generating an X-ray image using the digital signal, wherein the generating an X-ray image comprises:

acquiring a high-energy image and a low-energy image respectively obtained by X-ray of relatively high-energy and X-ray of relatively low-energy;

generating high-energy frequency component images for each of a plurality of frequency bands by decomposing the high-energy image;

generating low-energy frequency component images for each of a plurality of frequency bands by decomposing the low-energy image;

generating merged frequency component images by merging at least a portion of the high-energy frequency component images for each of the plurality of frequency bands and at least a portion of the low-energy frequency component images for each of the plurality of frequency bands, and generating a standard image using the merged frequency component images, wherein the high-energy frequency component images for each of the plurality of frequency bands comprise high-energy frequency component images for each of the plurality of frequency bands decomposed by a Fourier transform or a wavelet transform, wherein the low-energy frequency component images for each of the plurality of frequency bands comprise a plurality of low-energy frequency component images for each frequency bands decomposed by a Fourier transform or a wavelet transform, and wherein the merged frequency component images are generated by the merging of the high-energy frequency component images and the low-energy frequency component images for each frequency band and an inverse Fourier transform or an inverse wavelet transform thereof, wherein the high-energy frequency component images and the low-energy frequency component images are merged with each other for a pixel or for a patch having a plurality of pixels, and wherein when the high-energy frequency component images and the low-energy frequency component images are merged for each frequency band, the merging is performed by selecting a pixel or a patch of one of the high-energy frequency component images and the low-energy frequency component images of a corresponding frequency band that has a statistical value indicating a greater contrast to be merged.

* * * * *